US008846610B2

(12) United States Patent
Keith et al.

(10) Patent No.: US 8,846,610 B2
(45) Date of Patent: *Sep. 30, 2014

(54) METHODS FOR PREPARING PURIFIED LIPOPEPTIDES

(71) Applicant: Cubist Pharmaceuticals, Inc., Lexington, MA (US)

(72) Inventors: Dennis Keith, Montclair, NJ (US); Jan-Ji Lai, Westborough, MA (US); Chandrika Govardhan, Lexington, MA (US); Nazer Khalaf, Worcester, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/955,495

(22) Filed: Jul. 31, 2013

(65) Prior Publication Data

US 2014/0087425 A1  Mar. 27, 2014

Related U.S. Application Data

(63) Continuation of application No. 12/198,666, filed on Aug. 26, 2008, which is a continuation of application No. 11/108,380, filed on Apr. 18, 2005, now abandoned, which is a continuation-in-part of application No. 10/023,517, filed on Dec. 17, 2001, now abandoned, said application No. 11/108,380 is a continuation-in-part of application No. 10/024,701, filed on Dec. 17, 2001, now abandoned, said application No. 11/108,380 is a continuation-in-part of application No. 10/024,405, filed on Dec. 18, 2001, now abandoned.

(60) Provisional application No. 60/256,268, filed on Dec. 18, 2000, provisional application No. 60/274,741, filed on Mar. 9, 2001, provisional application No. 60/341,315, filed on Dec. 13, 2001, provisional application No. 60/340,525, filed on Dec. 13, 2001.

(51) Int. Cl.
    *A61K 38/12* (2006.01)
    *C07K 7/54* (2006.01)
    *C07K 11/02* (2006.01)
    *C07K 7/08* (2006.01)
    *C07K 7/66* (2006.01)
    *A61K 38/00* (2006.01)

(52) U.S. Cl.
    CPC . *C07K 7/66* (2013.01); *C07K 11/02* (2013.01); *C07K 7/08* (2013.01); *A61K 38/00* (2013.01)
    USPC ............................................ 514/2.9; 530/317

(58) Field of Classification Search
    CPC .................................. A61K 38/12; C07K 7/64
    See application file for complete search history.

(56) References Cited

U.S. PATENT DOCUMENTS

| 3,773,919 A | 11/1973 | Boswell et al. |
| 4,331,594 A | 5/1982 | Hamill et al. |
| RE31,396 E | 9/1983 | Hamill et al. |
| 4,439,425 A | 3/1984 | Tarcsay et al. |
| 4,482,487 A | 11/1984 | Abbott et al. |
| 4,485,045 A | 11/1984 | Regen |
| 4,522,811 A | 6/1985 | Eppstein et al. |
| 4,524,135 A | 6/1985 | Abbott et al. |
| 4,537,717 A | 8/1985 | Abbott et al. |
| 4,544,545 A | 10/1985 | Ryan et al. |
| 4,600,526 A | 7/1986 | Gallot et al. |
| RE32,310 E | 12/1986 | Debono |
| RE32,311 E | 12/1986 | Debono |
| RE32,333 E | 1/1987 | Hamill |
| RE32,455 E | 7/1987 | Hamill |
| 4,800,157 A | 1/1989 | Eaton et al. |
| 4,874,843 A | 10/1989 | Baker |
| 4,882,164 A | 11/1989 | Ferro |
| 4,885,243 A | 12/1989 | Huber et al. |
| 4,994,270 A | 2/1991 | Boeck et al. |
| 5,013,556 A | 5/1991 | Woodle et al. |
| 5,039,789 A | 8/1991 | Fukuda et al. |
| 5,271,935 A | 12/1993 | Franco et al. |
| 5,336,756 A | 8/1994 | Schwartz et al. |
| 5,387,670 A | 2/1995 | Roy et al. |

(Continued)

FOREIGN PATENT DOCUMENTS

| EP | 0095295 | 11/1983 |
| EP | 0178152 | 4/1986 |

(Continued)

OTHER PUBLICATIONS

Akins, R. L., et al., "In vitro activities of daptomycin, arbekacin, vancomycin and gentamicin alone and/or in combination against glycopeptide intermediate-resistant *Staphylococcus aureus* in an infection model." Antimicrobial Agents and Chemotherapy 44(7), 1925-1929 (Jul. 2000).

Akins R. L., et al., "Pharmacodynamics of daptomycin (D) against vancomycin-resistant *Enterococcus faecium* (VREF) and methicillin-resistant *Staphylococcus aureus* (MRSA) in an in vitro infection model with simulated endocardial vegetations (SEVs)." American Society of Microbiology Poster #A-19 (2000).

Alborn, W.E. Jr., et al., "Daptomycin disrupts membrane potential in growing *Staaphylococcus aureus*." Antimicrobial Agents and Chemotherapy 35(11), 2282-2287 (Nov. 1991).

Allen, N.E., "LY146032 inhibits the biosynthesis of cell wall peptidoglycan in gram-positive bacteria." Program and Abstracts of the Twenty-Fourth Interscience Conference on Antimicrobial Agents and Chemotherapy p. 281, Abstract 1081 (Oct. 8-10, 1984).

(Continued)

*Primary Examiner* — Christina Bradley
(74) *Attorney, Agent, or Firm* — Lathrop & Gage LLP; Brian C. Trinque

(57) ABSTRACT

The present invention relates to crystalline and crystal-like forms of lipopeptides, including daptomycin, a lipopeptide antibiotic with potent bactericidal activity against gram-positive bacteria, including strains that are resistant to conventional antibiotics. The present invention relates to methods of purifying lipopeptides, including daptomycin, a lipopeptide antibiotic with potent bactericidal activity against gram-positive bacteria, including strains that are resistant to conventional antibiotics. The present invention also relates to pharmaceutical compositions comprising the purified form of the lipopeptide and methods of using these compositions.

20 Claims, 15 Drawing Sheets

(56) References Cited

U.S. PATENT DOCUMENTS

| | | | |
|---|---|---|---|
| 5,527,534 | A | 6/1996 | Myhling |
| 5,529,782 | A | 6/1996 | Staab |
| 5,573,936 | A | 11/1996 | Kreuzman et al. |
| 5,602,097 | A | 2/1997 | Edwards |
| 5,629,288 | A | 5/1997 | Lattrell et al. |
| 5,696,084 | A | 12/1997 | Lartey et al. |
| 5,763,397 | A | 6/1998 | Vertesy et al. |
| 5,912,226 | A | 6/1999 | Baker et al. |
| 5,928,666 | A | 7/1999 | Farinas et al. |
| 5,932,015 | A | 8/1999 | Yoneda et al. |
| 5,955,509 | A | 9/1999 | Webber et al. |
| 5,959,108 | A | 9/1999 | Bauer et al. |
| 5,965,747 | A | 10/1999 | Brands et al. |
| 5,969,156 | A | 10/1999 | Briggs et al. |
| 5,972,331 | A | 10/1999 | Reichert et al. |
| 5,972,551 | A | 10/1999 | Miyauchi et al. |
| 6,017,562 | A | 1/2000 | Kaufman et al. |
| 6,017,921 | A | 1/2000 | Kennedy et al. |
| 6,043,303 | A | 3/2000 | Kobayashi et al. |
| 6,194,383 | B1 | 2/2001 | Hammann et al. |
| 111,311 | A1 | 8/2002 | Govardhan et al. |
| 142,948 | A1 | 10/2002 | Oleson, Jr. et al. |
| 6,468,967 | B1 | 10/2002 | Oleson, Jr. et al. |
| 6,696,412 | B1 | 2/2004 | Kelleher et al. |
| 6,794,490 | B2 | 9/2004 | Hill et al. |
| 6,852,689 | B2 | 2/2005 | Oleson, Jr. et al. |
| RE39,071 | E | 4/2006 | Baker et al. |
| 8,003,673 | B2 | 8/2011 | Alder et al. |
| 8,058,238 | B2 | 11/2011 | Kelleher et al. |
| 8,129,342 | B2 | 3/2012 | Kelleher et al. |
| 8,309,061 | B2 | 11/2012 | Chaudry et al. |
| 8,431,539 | B2 | 4/2013 | Palepu et al. |
| 2003/0045484 | A1 | 3/2003 | Keith et al. |
| 2003/0045678 | A1 | 3/2003 | Keith et al. |
| 2005/0009747 | A1 | 1/2005 | Kelleher et al. |
| 2005/0027113 | A1 | 2/2005 | Miao et al. |
| 2006/0014674 | A1 | 1/2006 | Keith et al. |
| 2007/0128694 | A1 | 6/2007 | Baltz et al. |
| 2009/0197799 | A1 | 8/2009 | Keith et al. |
| 2010/0041589 | A2 | 2/2010 | Keith et al. |
| 2012/0149062 | A1 | 6/2012 | Kelleher et al. |
| 2012/0270772 | A1 | 10/2012 | O'Connor et al. |

FOREIGN PATENT DOCUMENTS

| | | |
|---|---|---|
| EP | 0 294 990 A2 | 12/1988 |
| EP | 0 337 731 A2 | 10/1989 |
| EP | 0 386 951 A2 | 9/1990 |
| EP | 0 511 866 A2 | 11/1992 |
| EP | 0629636 | 12/1994 |
| EP | 1252179 | 10/2002 |
| EP | 1115417 | 9/2006 |
| JP | 64-047388 | 2/1989 |
| JP | 4-224197 | 8/1992 |
| JP | 5-239090 | 9/1993 |
| JP | 5-271284 | 10/1993 |
| JP | 7-506098 | 7/1995 |
| WO | WO 93/21207 | 10/1993 |
| WO | WO 9822107 | 5/1998 |
| WO | WO9927954 | 6/1999 |
| WO | WO9927957 | 6/1999 |
| WO | WO 9930728 | 6/1999 |
| WO | WO 99/42191 | 8/1999 |
| WO | WO9940113 | 8/1999 |
| WO | WO9943700 | 9/1999 |
| WO | WO 99/55310 | 11/1999 |
| WO | WO0018419 | 4/2000 |
| WO | WO 01/44271 A2 | 6/2001 |
| WO | WO 01/44272 A2 | 6/2001 |
| WO | WO 01/44274 | 6/2001 |
| WO | WO 01/53330 A2 | 7/2001 |
| WO | WO 02/056829 A2 | 7/2002 |
| WO | WO 02/059145 | 8/2002 |
| WO | WO 03/063745 | 8/2003 |
| WO | WO 2004/104019 | 12/2004 |

OTHER PUBLICATIONS

Allen, N.E., et al., "Inhibition of membrane potential-dependent amino acid transport by daptomycin." Antimicrobial Agents and Chemotherapy 35 (12), 2639-2642 (Dec. 1991).

Allen, N.E., et al., "Inhibition of peptidoglycan biosynthesis in gram-positive bacteria by LY146032." Antimicrobial Agents and Chemotherapy 31(7), 1093-1099 (Jul. 1987).

Anaizi, N., "Once-daily dosing of aminoglycosides a consensus document." Int. J. Clin. Pharm. Ther. 35(6), 223-226 (1997).

Andreasen, James R. Jr., et al., "Salinomycin toxicosis in male breeder turkeys." Avian Diseases 39, 638-642 (1995).

Appleman, M.D., et al., "In vitro activities of daptomycin (CidecinTM), linezolid, quinupristin/dalfopristin, ziracin, and cancomycin against 255 unique clinical isolates of oxacillin-resistant *Staphylococcus aureus* isolated over four years (196-1999)." Interscience Conference on Antimicrobial Agents and Chemotherapy Poster #2291 (2000).

Arbeit, et al., "Safety and Efficacy of Daptomycin for Treatment of Complete Skin and Skin Structure Infections." Clinical Infectious Diseases 38:1673-81(2004).

Aronoff, George R., et al., "Aminoglycoside accumulation kinetics in rat renal parenchyma." Antimicrobial Agents and Chemotherapy 23(1), 74-78 (Jan. 1983).

Aronoff, George R., et al., "LY146032 kinetics in normal subjects and patients with renal insufficiency." Program and Abstracts of the Twenty-Fourth Interscience Conference on Antimicrobial Agents and Chemotherapy p. 132, Abstract 125 (Oct. 23-26, 1988).

Baltz, Richard H., "Lipopeptide Antibiotics Produced by *Streptomyces roseosporus* and *Streptomyces fradiae*." Biotechnol. Antibiotics 2d ed, 415-435 (1997).

Barclay, Murray L., et al., "What is the evidence for once-daily aminoglycoside therapy?" Clin. Pharmacokinet. 27 (1), 32-48 (1994).

Barry, Arthur L., et al., "In vitro activities of daptomycin against 2.789 clinical isolates from 11 North American medical centers." Antimicrobial Agents and Chemotherapy 38(2), 189-194 (Feb. 1994).

Beauchamp, Denis, et al,. "Effects of daptomycin and vancomycin on tobramycin nephrotoxicity in rats" Antimicrobial Agents and Chemotherapy 34, 139-147 (1990).

Beauchamp, Denis, et al., "Subcellular distribution of daptomycin given alone or with tobramycin in renal proximal tubular cells." Antimicrobial Agents and Chemotherapy 38(2), 189-194 (Feb. 1994).

Benson, Constance A., et al., "Comparative in-vitro activity of LY146032 a new peptolide, with vancomycin and eight other agents against gram-positive organisms." J. Antimicrobial Chemotherapy 20, 191-196 (1987).

Benvenuto, M, et al., "Pharmacokinetics and Tolerability of Daptomycin at Does up to 12 Milligrams per Kilogram of Body Weight once Daily in Healthy Volunteers," Antimicrobial Agents and Chemotherapy vol. 50, No. 10, pp. 3245-3249, (Oct. 2006).

Bergan, Tom, "Kinetics of tissue penetration." Scand. J. Infect Dis. Suppl. 14, 36-46 (1978).

Bergan, Tom, "Pharmacokinetics of tissue penetration of antibiotics." Rev. Infections Diseases 3(1), 45-66 (Jan.-Feb. 1981).

Bergeron, Michel G., "Tissue penetration of antibiotics." Clin. Biochem. 19, 90-100 (Apr. 1986).

Bernard, et al., "Pharmacokinetics and Suction Blister Fluid Penetration of a Semisynthetic Injectable Streptogramin RP59500 (RP 57699/RP54476)." Eur. J. Clin. Microbiol. Infect. Dis. 13, 768-771 (1994).

Bingen, E., et al., "Bactericidal activity of vancomycin, daptomycin, ampicillin and aminoglycosides against vancomycin-resistant *Enterococcus faecium*." J. Antimicrobial Chemotherapy 26, 619-626 (1990).

Black, H.R., et al., "Preliminary pharmacology and pharmacokinetics of LY146032, a new peptolipide antibiotic." Program and

(56) References Cited

OTHER PUBLICATIONS

Abstracts of the 1986 Interscience Conference on Antimicrobial Agents and Chemotherapy p. 261, Abstract 894 (1986).
Blenkharn, J.I., et al., "Comparitive in vitro activity of daptomycin (LY146032) and vancomycin against gram-positive cocci determined using a pharmacoinetic model." Eur. J. Clin. Microbial. Infect. Dis. 8, 734-737 (1989).
Boaretti, Marzia, et al., "Identification of daptomycin-binding proteins in the membrane of *Enterococcus hirae*." Antimicrobial Agents and Chemotherapy 39(9), 2068-2072 (Sep. 1995).
Boaretti, Marzia, et al., "The activity of daptomycin on *Enterococcus faecium* protoplasts: Indirect evidence supporting a novel mode of action on lipoteichoic acid synthesis." J. Antimicrobial Chemotherapy 31, 227-235 (1993).
Bocci, Veliio, "Catabolism of therapeutic proteins and peptides with implications for drug delivery." Advanced Drug Delivery Rev. 4, 149-169 (1990).
Bolton, Charles F., et al., "Critically Ill polyneuropathy: Electrophysiological studies and differentiation from Guillain-Barre Syndrome." J. Neurol, Neurosug. Psychiatry 49, 563-573 (1986).
Boxenbaum, et al., "Interspecies Pharmacokinetic Scaling, Biological Design and Neoteny." Adv. in Drug Res. 19, 139-196 (1990).
Brown, S.D., et al., "In vitro activity of daptomycin (CidecinTM) against contemporary gram-positive clinical bacterial isolates from 11 North American Medical Centers (NAMC)." European Congress of Clinical Microbiology and Infectious Dieases Poster #P90:5/5 (2000).
Bryant, R.E., et al., "Effect of abscess milieu on bacterial actvity of LY146032 against *Staphylococci*." Eur. J. Clin. Microbiol. 6, 186-188 (1987).
Bush, Larry M., et al., "Daptomycin (LY146032) treatment of experimental Enterococcal endocarditis." Antimicrobial Agents and Chemotherapy 32, 877-881 (1988).
Bush, Larry M., et al., "In vitro postantibiotic effect of daptomycin (LY146032) against *Enterococcus faecalis* and methicillin-susceptible and methicillin-resistant *Staphylococcus aureus* strains." Antimicrobial Agents and Chemotherapy 33, 1198-1200 (Aug. 1989).
Canepari, Pietro, et al., "Lipoteichoic acid as a new target for activity of antibiotics: Mode of action of daptomycin (LY146032)." Antimicrobial Agents and Chemotherapy 34, 1220-1226 (Jun. 1990).
Canton!, L., et al., "Comparative efficacy of daptomycin, vancomycin, and cloxacillin for the treatment of *Staphylococcus aureus* endocarditis in rats and role of test conditions in this determination." Antimicrobial Agents and Chemotherapy 34, 2348-2353 (1990).
Caron, et al., "Daptomycin or Teicoplanin in Combination with Gentamicin for Treatment of Experimental Endocarditis Due to a Highly Glycopeptide-Resistant Isolate of *Enterococcus faecium*." Antimicrobial Agents and Chemotherapy 36, 2611-2616 (1992).
Carrier, Danielle, et al., "Modulation of phospholipase A2 activity by aminoglycosides and daptomycin: A fourier transform infrared spectroscopic study." Biochem. 37, 7589-7597 (1998).
Confer, A.W., et al., "Light and electron microscopic changes in cardiac and skeletal muscle of sheep with experimental monensin toxicosis." Verterinary Pathology 20, 590-602 (1983).
Couture, Michele, et al., "Daptomucin may attenuate experimental tobramycin nephrotoxicity by electrostatic complexation to tobramycin." Antimicrobial Agents and Chemotherapy 38 (4), 742-749 (Apr. 1994).
Craig, W.A., "Once-daily versus multiple-daily dosing of aminoglycosides." J. Chemotherapy 7, 47-52 (1995).
De La Maza, Lorena, et al., "In vitro activities of daptomycin and oter antimicrobial agents against vancomycin-resistant gram-positive bacteria." Antimicrobial Agents and Chemotherapy 33(8), 1383-1384 (Aug. 1989).
Debbia, Eugenio, et al., "In vitro activity of LY146032 alone and in combination with other antibodies against gram-positive bacteria." Antimicrobial Agents and Chemotherapy 32(2), 279-281 (Feb. 1988).
Debruin, Michael F., "Efficacy and safety of daptomycin for the treatment of bacteremia and serious infections due to gram-positive bacteria." 4th Decennial International Conference on Nosocomial and Healthcare-Associated Infections Poster #594 P-S2-37 (Mar. 5-9, 2000).
Digranes, Asbjorn, et al., "In vitro activity of daptomycin against 297 staphylococcal isolates." Chemotherapy 36, 136-140 (1990).
Dong, Mei-Yan, et al., "Treatment of *Clostridium difficile* colitis in hamsters with a lipopeptide antibiotic LY146032." Antimicrobial Agents and Chemotherapy 32, 1135-1136 (1987).
Bayer, A. et al.; LY146032 Compared with Pencillin G in Experimental Aortic Valve Endocarditis Caused by Group G Streptococci; Antimicrobial Agents and Chemotherapy, vol. 32, No. 1; Jan. 1988, p. 141-143.
Cubicin® (daptomycin for injection) Label 1004—Sep. 2003.
Lasic, Mixed Micellers in Drug Delivery; Nature 1992, vol. 355, pp. 279-282.
Lasic, Novel Applications of Liposomes; Trends in Biotechnology 1998, vol. 16, pp. 307-321.
Yakimov et al., "Characterization of a New Lipopeptide Surfactant Produced by Thermotolerant and Halotolerant Subsurface *Bacillus licheniformis* BAS50," Applied and Environmental Microbiology 1995; vol. 61, pp. 1706-1713.
Lin et al., General Approach for the Development of High-performance Liquid Chromatography Methods for Biosurfactant Analysis and Purification; Journal of Chromatography 1998, vol. 825, pp. 149-159.
Molloy, et al., Abstract,"Structure & Anhydro-Daptomycin and Iso-Daptomycin," ACS 200th Meeting, 1990.
Molloy, et al., Poster, "Structure & Anhydro-Daptomycin and Iso-Daptomycin," ACS 200th Meeting, 1990.
Mulligan et al., Recovery of Biosurfactants by Ultrafiltration; J. Chem. Tech. Biotechnology 1990, vol. 47, pp. 23-29.
Sweadner et al., "Filter Removal of Endotoxin (Pyrogens) in Solution in Different States of Aggregation," Applied and Environmental Microbiology 1977; vol. 34, pp. 382-385.
Thimon et al., "Surface-Active Properties of Antifungal Lipopeptides Produced by *Bacillus substillis*," J. Am. Oil Chem. Soc. 1992, vol. 69, pp. 92-93.
Schott, Colloidal Dispersions; Remington: The Science and Practice of Pharmacy; vol. 1, 19th Edition, 1995; pp. 252-277, Mack Publishing Company; Easton, Pennsylvania USA.
Sterling; "Membrane-Based System Combines Selective Separation with High-Volume Throughput," Genetic Engineering News; vol. 19; No. 20; Nov. 15, 1999; pp. 1, 34.
Supersaxo et al., "Mixed Micelles as Proliposomal, Lymphotropic Drug Carrier," Pharmaceutical Research 1991; vol. 8, pp. 1286-1291.
Cubicin® (daptomycin for injection) Label 1004 -1—Revised Aug. 2004.
Cubicin® (daptomycin for injection) Label 1004 -2—Revised Jun. 2005.
Cubicin® (daptomycin for injection) Label 1004 -10-1—Aug. 2010.
Lin, S. C. et al.; "Recovery and Purification of the Lipopeptide Biosurfactant of *Bacillus subtillis* by Ultrafiltration," Biotechology Techniques; vol. 11; No. 6; Jun. 1997; pp. 413-416.
Ramos, M. C., "Comparison of Daptomycin, Vancomycin, and Ampicillin-Gentamicin for Treatment of Experimental Endocarditis Caused by Penicillin-Resistant Enterococci," Antimicrobial Agents and Chemotherapy; vol. 36; No. 9; Sep. 1992, p. 1864-1869.
Lee, et al., "Effect of protein binding of daptomycin on MIC and antibacterial activity." Antimicrobial Agents and Chemotherapy 35, 2505-2508 (1991).
Leggett, J., et al., "Pharmacodynamic and pharmacokinetic parameters (PKPs) affecting activity of LY146032 against *Staphylococcus aureus*." Program and Abstracts of the 1986 Interscience Conference on Antimicrobial Agents and Chemotherapy p. 123, Abstract 154 (1987).
Li, T., et al., "In vivo efficacy of daptomycin against systemic infection induced by vancomycin-resistant *Enterococcus faecalis* (VRE) in the mouse." Interscience Conference on Antimicrobial Agents and Chemotherapy Abstract F-116 (Sep. 24-27, 1998).
Li, Tongchuan, et al., "Daptomycin efficacy against vancomycin-resistant *Enterococcus faecalis* (VRE)—induced pyelonephritis in

(56) References Cited

OTHER PUBLICATIONS the mouse." Interscience Conference on Antimicrobial Agents and Chemotherapy Poster #1003 (Sep. 26-29, 1999).
Li, Tongchuan, et al., "Effect of oral daptomycin on vancomycin-resistant *Enterococcus faecium* (VREF) gastrointestinal tract colonization in antibiotic treated mouse." Infectious Disease Society of America Meeting Abstract #244-Sa (Nov. 12-15, 1998).
Liebowitz, Lynne D., et al., "In vitro selection of bacteria resistant to LY146032, a new cyclic lipopeptide." Antimicrobial Agents and Chemotherapy 32(1), Jan. 24-26, 1988.
Louie, Arnold, et al., "Comparison of in vitro inhibitory and bactericidal activities of daptomycin (LY146032) and four reference antibiotics, singly and in combination, against gentamicin-susceptible and high-level-gentamicin-resistant enterococci." Chermotherapy 39, 302-310 (1993).
Louie, Arnold, et al., "Pharmacodynamics of daptomycin in a murine thigh model of *Staphylococcus aureus* infection." Antimicrobial Agents and Chemotherapy 45(3), 845-851 (Mar. 2001).
Louie, Arnold, et al., "The pharmacodynamics of daptomycin as determined for *Staphylococcus aureus* in a mouse thigh infection model." Interscience Conference on Antimicrobial Agents and Chemotherapy Poster #1770 (Sep. 26-29, 1999).
Low, et al., "Enterococci: Pathogens of the 90s." Euro. J. Sugery Suppl. 573, 19-24 (1994).
Lucas, Gregory M., et al., "Vancomycin-resistant and vancomycin-susceptible enterococcal bacteremia: Comparison of Clinical Features and Outcomes." Clinical Infectious Diseases 26, 1127-1133 (May 1998).
Lutz, H., et al., "Ototoxicity of vancomycin: An experimental study in guinea pigs." ORL J. Otorhinolaryngol. Relat. Spec. 53, 273-278 (1991).
Luu, Q.N., et al., "Treatment of chronic experimental *Staphylococcus aureus* osteomyelitis with LY146032 and vancomycin." Eur. J. Clin. Microbiol. Infect. Dis. 8, 562-563 (1989).
Mader, Jon T., et al., "Comparative evaluation of daptomycin (LY146032) and vancomycin in the treatment of experimental methicillin-resistant *Staphylococcus aureus* osteomyelitis in rabbits." Antimicrobial Agents and Chemotherapy 33, 689-692 (1989).
Malone, Donald A., et al., "Enterococcal bacteremia in two large community teaching hospitals." Am. J. Med. 81, 601-606 (Oct. 1986).
Markowitz, Sheldon M., et al., "Antimicrobial susceptibility and molecular epidemiology of beta-lactamse-producing, aminoglycoside-resistant isolates of *Enterococcus faecalis*." Antimicrobial Agents and Chemotherapy 35 (6), 1075-1080 (Jun. 1991).
Mengin-Lecreulx, Dominique, et al., "Inhibition of peptidoglycan biosynthesis in *Bacillus megaterium* by daptomycin." FEMS Microbiol. Ltrs. 69, 245-248 (1990).
Michiels, Marie-Jose, et al., "Differential increased survival of staphylococci and limited ultrastructural changes in the core of infected fibrin clots after daptomycin administration." Antimicrobial Agents and Chemotherapy 40, 203-211 (1996).
Miniter, Peggy M., et al., "Activity of LY146032 in vitro and in experimental enterococcal pyelonephritis." Antimicrobial Agents and Chemotherapy 31, 1199-1203 (1987).
Mobarakai, Neville, et al., "Bacterial activities of peptide antibiotics against multidrug-resistant *Enterococcus faecium*." Antimicrobial Agents and Chemotherapy 38(2), 385-387 (Feb. 1994).
Moellering, et al., "The Efficacy and Safety of Quinupristin/Dalfopristin for the Treatment of Infections Caused by Vancomycin-Resistant *Enterococcus faecium*." J. Antimicrob. Chemotherapy 44, 251-261 (1999).
Moise, Pamela A., et al, "Safety and Clinical Outcomes when Utilizing High-Dose (>_3 mg/kg) Daptomycin Therapy." The Annals of Pharmacotherapy43, 1211-1219, Jul./Aug 2009.
Morris, Charles M., "Effect of polymyxin B nonapeptide on daptomycin permeability and cell surface properties in *Pseudomonas aeruginosa, Escherichia coli*,and *Pasteurella multocida*." J. Antibiotics 48(1), 67-72 (Jan. 1995).

Mouton, R. Peter, et al., "LY146032: Activity and resistance development in vitro." J. Antimicrobial Chemotherapy 20, 513-517 (1987).
Nicolau, David P., et al., "Experience with a once-daily aminoglycoside program administered to 2,184 adult patients." Antimicrobial Agents and Chemotherapy 39(3), 650-655 (Mar. 1995).
Nord, C.E., et al., "LY14032 treatment of *Clostridium difficile* colitis in hamsters." Eur. J. Clin. Microbiol. 6, 686 (1987).
Novilla, M.N., "The veterinary importance of the toxic syndrome induced by Ionophores." Vet. Hum. Toxicol. 34(1), 66-70 (Feb. 1992).
Ole-Mapenay, et al., "Aspects of the Pharmacokinetics of Doxycycline Given to Healthy and Pneumonic East African Dwarf Goats by Intramuscular Injection." Veterinary Res. Comm. 21, 453-462 (1997).
Oleson, F.B., et al., "Once-daily dosing decreases toxicity of daptomycin." Toxicological Sciences, Academic Press, San Diego, FL, US vol. 44, Jan. 1, 1999, p. 322.
Oleson, F.B., et al., "Once-daily dosing in dogs optimizes daptomycin safety." Antimicrobial Agents and Chemotherapy 44, 2948-2953 (2000).
Oleson, Rick, et al., "Once-daily dosing decreases toxicity of daptomycin." 38th Annual Meeting Society of Toxicology Poster #1520 (Mar. 14-18, 1999).
Oleson, Rick, et al. "Once-daily dosing decreases toxicity of daptomycin." 9th European Congress of Clinical Microbiology and Infectious Diseases Poster #P0957A (Mar. 21-24, 1999).
Oleson, Rick, et al., "Separate mechanisms for the schedule dependence of daptomycin's toxicity and efficacy." Sierra Biomedical Incorporated Annual Biotech Symposium Presentation (Jun. 7 & 8, 1999).
Oliver, N., et al., "In vitro studies on resistance to the lipopeptide antibiotic daptomycin." Interscience Conference on Antimicrobial Agents and Chemotherapy Poster #F-117 (1998).
Pascual, A., et al., "Effect of Polyurethane Catheters and Bacterial Biofilms on the In-Vitro Activity of Antimicrobials Against *Staphylococcus epidermidis*," Journal of Hospital Infection 24, pp. 211-218, (1993).
Periti, P., "Preclinical and clinical evaluation of once-daily aminoglycoside chemotherapy." J. Chemotherapy 7 (4), 311-337 (1995).
Physician's Desk Reference. "Azactam for Injection." Bristol-Myers Squibb Co., 779-782, 2004.
Pittet, Didler, et al., "Microbiological Factors Influencing the Outcome of Nosocomial Bloodstream Infections: A 6-year validated, population-based model." Clinical Infectious Diseases 24, 1068-1078 (Jun. 24, 1997).
Pohlod, Donald J., "In-vitro susceptibility of gram-positive cocci to LY146032 teicoplanin, sodium fusidate, vancomycin, and rifampicin." J. Antimicrobial Chemotherapy 20, 197-202 (1987).
Powell, S.H., "Once-daily vs. continuous aminogylcoside dosing; efficacy and toxicity in animal and clinical studies of gentamicin, netilmicin, and tobramycin." J. of Infectious Diseases 147(5), 918-932 (May 1983).
Preston, Sandra L., "Pharmacodynamics of levofloxacin: A new paradigm for early clinical trials." JAMA 279(2), 125-129 (Jan. 14, 1998).
Prieur, et al., "Clinical toxicologic evaluation of cancer chemotherapeutic agents: Protocols of the laboratory of toxicology." Cancer Chemotherapy Reports 4, 1-30 (1973).
Pryka, et al., "Clinical pharmacokinetics of daptomycin." DICP, Annals of Pharmacotherapy 24/3, 255-256 (1990).
Remington's Pharmaceutical Sciences, 17th ed., 1176-1212 (1985).
Rice, Louis B., et al., "In vitro synergism between daptomycin and fosfomycin against *Enterococcus faecalis* isolates with high-level gentamicin resistance." Antimicrobial Agents and Chemotherapy 33(4), 470-473 (Apr. 1989).
Rice, Louis B., et al., "In vivo activity of the combination of daptomycin and fosfomycin compared with daptomycin alone against a strain of *Enterococcus faecalis* with high-level gentamicin resistance in the rat endocarditis model." Diagn. Microbiol. Infect. Dis. 15, 173-176 (1992).
Rotschafer, et al., "Therapeutic update on glycopeptide and lipopeptide antibiotics." Pharmacotherapy 8, 211-219 (1988).

(56) References Cited

OTHER PUBLICATIONS

Rowland, Malcom, et al., "Interacting Drugs." Clinical Pharmacokinetics—Concepts and Applications, Ch. 17, 272-273 (1995).
Akins, R.L., et al., "Activity of Daptomycin (D), Arbekacin (A), Vancomycin (V) and Gentamicin (G) against two clinical strains of Vancomycin-Intermediate resistant *Staphylococcus Aureus* (VISA) in an in vitro pharmacodynamic infection model. (IVPM)." Interscience Conference on Antimicrobial Agents and Chemotherapy Poster #1771 (1999).
Akins, R.L., et al., "Bactericidal activities of two daptomycin regimens against clinical strains of glycopeptide intermediate-resistant *Staphylococcus aureus*, vancomycin-resistant *Enterococcus faecium*, and methicillin-resistant *Staphylococcus aureus* isolates in an in vitro phamacodynamic model with simulated endocardial vegetations". Antimicrobial Agents and Chemotherapy 45(2), 454-459 (Feb. 2001).
Miao et al., "Daptomycin biosynthesis in *Streptomyces roseosporus*: cloning and analysis of the gene cluster and revision of peptide stereochemistry," Microbiology 2005, vol. 151 (5), 1507-23.
Debono, et al., "A21978C, A Complex of New Acidic Peptide Antibiotics: Isolation, Chemistry, and Mass Spectral Structure Elucidation," The Journal of Antibiotics 1987, vol. XL (6), p. 761-77.
Lodish et al., Molecular Cell Biology (ed. by J. Darnell, H. Lodish, and D. Baltimore, Scientific American Books, Inc., New York: 1986), Chapter 3, p. 53.
Johnson et al., ICAA 1987, poster 161, 1 page.
McKindley et al., "Drug Use in the Critically Ill Patient with Renal Dysfunction-Application of the DREM System," Infectious Diseases in Critical Care Medicine Biotechnology of Antibiotics (ed. B.A. Cunha, New York: Marcel Dekker, Inc., 1998) Chapter 41, pp. 781-801.
Mariani et al., Development of decreased susceptibility to daptomycin and vancomycin in a *Staphylococcus aureus* strain during prolonged therapy; Journal of Antimicrobial Chemotherapy 2013, p. 481-83.
Janson et al., Protein Purification: Principles, High Resolution Methods, and Applications; Ch. 1: Introduction to Protein Purification; John Wiley & Sons, Inc., 1998; pp. 3-48, p. 80, and pp. 125-126.
Matthews et al., IDSA poster, 2001.
Shaw, D.J., "Liquid-Gas and Liquid-Liquid Interfaces," Introduction to Colloid and Surface Chemistry, Butterworth-Heinemann Ltd., 1989, pp. 49-90.
Mchenney et al., Molecular Cloning and Physical Mapping of the Daptomycin Gene Cluster from *Streptomyces roseosporus*; Journal of Bacteriology, 1998, vol. 180, pp. 143-151.
Remington: The Science and Practice of Pharmacy, (19th edition, Mack Publishing Company, 1985), pp. 539-551, 1529-1530, 1549-1550, and 1558.
Moise et al., susceptibility relationship between vancomycin and daptomycin in *Staphylococcus aureus*: facts and assumptions; Lancet Infect. Dis. 2009, vol. 9, pp. 617-624.
Selwyn, et al.; Infections (Excluding AIDS) of Injection Drug Users; Harrison's Principles of Internal Medicine; Fauci, et al. eds., 14th ed., McGraw-Hill, 1998, pp. 831-832, and 847.
Lee et al., Program and Abstracts of the ICAAC 1991, Abstract No. 865.
Patel et al., An Association bettween Reduced Susceptibility to Daptomycin and Reduced Susceptibility to Vancomycin in *Staphylococcus aureus*; Clinical Infectious Diseases; Correspondence to the Editor; Jun. 1, 2006, vol. 42, pp. 1652-1653.
Mutschler et al., Drug Actions: Basic Principles and Therapeutic Aspects; Ch. 2: Pharmacokinetics; Medpharm Scientific Publishers, Stuttgart, Germany (1995); p. 5, 47 pages.
Sader et al., Nine-Hospital Study Comparing Broth Microdilution and Etest method Results for Vaqncomycin and Daptomycin against Methicillin-Resistant *Staphylococcus aureus*; Antimicrobial Agents and Chemotherapy, 2009, vol. 53, pp. 3162-3165.

Ebert et al., Pharmacodynamics Properties of Antibiotics: Application to Drug Monitoring and Dosage Regimen Design; Infection Control and Hospital Epidemiology; 1990, 11(6), pp. 319-326.
Sader et al., Update on the In Vitro Activity of Daptomycin Tested against 17,193 Gram-positive Bacteria Isolated from European Medical Centers (2005-2007); Journal of Chemotherapy 2009, vol. 21, pp. 500-506.
Sakoulas et al., Clinical Outcomes of Patients Receiving Daptomycin for the Treatment of *Staphylococcus aureus* Infections and Assessment of Clinical Factors for Daptomycin Failure: A Retrospective Cohort Study Tuilizing the Cubicin Outcomes Registry and Experience; Clinical Therapeutics, 2009, vol. 31, pp. 1936-1945.
Silverman et al., Inhibition of Daptomycin by Pulmonary Surfactant: In Vitro Modeling and Clinical Impact; The Journal of Infectious Disease; 2005, vol. 191, pp. 2149-2152.
Schnellmann et al.; Cassarett and Douls Toxicology: The Basic Science of Poisons; Chapter 14: Toxic Responses of the Kidney; (5th ed.) (1996), pp. 491-514.
Benoit et al. "Destruction and regeneration of skeletal muscle after treatment with a local anesthetic, bupivacaine (Marcaine®)," J Anat. 1970, vol. 107, pp. 547-556.
Cubist Pharmaceuticals, Press Release, Feb. 5, 2008, Lexington, MA.
Steenbergen et al., Daptomycin: a lipopeptide antibiotic for the treatment of serious Gram-positive infections; Journal of Antimicrobial Chemotherapy, 2005, vol. 55, pp. 283-288.
Horowitz et al., Isolation and Characterization of a Surfactant Produced by *Bacillus licheniformis* 86; Journal of Industrial Microbiology 1990, vol. 6, pp. 243-248.
Tenover et al., Characterisation of a *Staphylococcus aureus* strain with progressive loss of susceptibility to vancomycin and daptomycin during therapy; International Journal of Antimicrobial Agents; 2009, p. 564-68.
U.S. Appl. No. 61/243,402, filed Sep. 17, 2009 (Priority Document for WO2011035108).
Auwera et al., Ex-vivo study of serum bactericidal titers and kiilling rates of daptomycin (LY146032) combined or not combined with amikacin compared with those of vancomycin; Antimicrobial Agents and Chemotherapy; 1989, vol. 33, pp. 1783-1790.
Barry et al., In vitro activities of daptomycin against 2,789 clinical isolates from 11 North American Medical Centers; Antimicrobial Agents and Chemotherapy; 2001, vol. 45, pp. 1919-1922.
U.S. Appl. No. 61/263,695, filed Nov. 23, 2009 (Priority Document for WO2011035108 and WO2011062676).
U.S. Appl. No. 61/371,802, filed Aug. 9, 2010 (Priority Document for WO2011062676).
Cubist Pharmaceutical, Inc. v. Hospira, Inc., No. 1:12cv367 (D. Mass. Filed Mar. 21, 2012) (Def. Hospira, Inc. Preliminary Invalidity Contentions).
Fostel, et al., "Emerging Novel Antifungal Agents," DDT; vol. 5; No. 1; Jan. 2000; pp. 25-32.
Caballero_Granado et al., Case-control Study of Risk Factors for the Development of Enterococcal Bacteremia; Eur. J. Clin. Microbiol. Infect. Dis. 2001, vol. 20, p. 83-90.
Desai et al., Microbial Production of Surfactants and Their Commercial Potential; Microbiology and Molecular Biology Reviews 1997, vol. 61, pp. 47-64.
U.S. Appl. No. 10/960,435 (Abandoned), filed Oct. 7, 2004.
Chaftari et al.; Efficacy and safety of daptomycin in the treatment of Gram-positive catheter-related bloodstream infections in cancer patients; International Journal of Antimicrobial Agents; 2010, vol. 36, pp. 182-186.
U.S. Appl. No. 13/185,191 (Abandoned), filed Jul. 18, 2011.
Crompton et al., Outocmes with daptomycin in the treatment of *Staphylococcus aureus* infections with a range of vancomycin MICs; Journal of Antimicrobial Chemotherapy; 2010, vol. 65, pp. 1784-1791.
Cubicin label, Nov. 2010; 34 pages.
Cui et al., Correlation between Reduced Daptomycin Susceptibility and Vancomycin Resistance in Vancomycin-Intermediate *Staphylococcus aureus*; Antimicrobial Agents and Chemotherapy; 2006, vol. 50, pp. 1079-1082.
Cunha et al., Daptomycin resistance and treatment failure following vancomycin for methicillin-resistant *Staphylococcus aureus*

(56) References Cited

OTHER PUBLICATIONS (MRSA) mitral valve acute bacterial endocarditis (ABE); Eur. J. Clin. Microbiol. Infect. Dis.; 2009, vol. 28, pp. 831-833.

Davis et al., Daptomycin versus Vancomycin for Complicated Skin and Skin Structure Infections: Clinical and Economic Outcomes, Pharmacotherapy, 2007, vol. 27, pp. 1611-1618.

U.S. Appl. No. 06/658,979 (Abandoned), filed Oct. 9, 1984.

U.S. Appl. No. 07/060,148 (Abandoned), filed Jun. 10, 1987.

Debruin. Michael F., Efficacy and safety of daptomycin for the treatment of bacteremia and serious infections due to gram-positive bacteria; 4th Decennial International Conference on Nosocomial and Healthcare-Associated Infections; Poster #594 P-S2-37 (Mar. 5-9, 2000), 14 pages.

DuCruix, et al., Crystallization of Nucleic acids and Proteins, A Practical Approach, 2d ed., 1999, pp. 92-95, 4 pages.

Forward et al., Comparative activity of daptomycin and teicoplanin against enterococci isolated from blood and urine, Can. J. Infect. Dis., 1992, vol. 3, pp. 173-178.

Rybak, et al., "Pharmacokinetics and bactericidal rates of daptomycin and vancomycin in intravenous drug abusers being treated for gram-positive endocarditis and bacteremia." Antimicrobial Agents and Chemotherapy 36, 1109-1114 (1992).

Rybak, Michael J., et al., "Bactericidal killing rate and pharmacokinetics of daptomycin and vancomycin in intravenous drug abusers being treated for *Staphylococcus aureus* endocarditis." Pharmacotherapy 11(1), 98 (1991).

Rybak, Michael J., et al., "Comparative in vitro activity of daptomycin versus vancomycin, linezolid, and synercid against methicillin-resitant and susceptible staphylococci, vancomycin-intermeditate suceptible *Staphylococcus aureus* (VISA) and vancomycin-susce." Interscience Conference on Antimicrobial Agents and Chemotherapy Abstract C-146 (1998).

Rybak, Michael J. et al. In vitro activities of daptomycin, vancomycin, linezolid, and quinupristin-dalfopristin against staphylococci and enterococci, including vancomycin-intermediate and resistant strains. Antimicrobial Agents and Chemotherapy 44(4), 1062-1066 (Apr. 2000).

Rybak, Michael J., et al., "Teicoplanin pharmacokinetics in burn patients and intravenous drug abusers." Antimicrobial Agents and Chemotherapy 44(4), 1062-1066 (Apr. 2000).

Rybak, Michael J., et al., "Vancomycin pharmacokinetics in burn patients and intravenous drug abusers." Antimicrobial Agents and Chemotherapy 34(5), 792-795 (May 1990).

Safdar, N., et al., "In-vivo pharmacodynamic activity of daptomycin (DAP) against multiple bacterial pathogens." Interscience Conference on Antimicrobial Agents and Chemotherapy 1999, Poster #1769.

Safdar, N., et al., "In-vivo pharmacodynamics of daptomycin (DAP)." Infectious Disease Society of America Abstract (Nov. 1999).

Salles, Monica S., "Ionophore Antibiotic (Narasin) Poisoning in Rabbits." Vet. Human Toxicol. 36(5), 437-444 (Oct. 1994).

Sapico, Francisco L., et al., "LY146032, alone and in combination with gentamicin, for the treatment of enterococcal pyelonephritis in the rat model." Antimicrobial Agents and Chemotherapy 32, 81-83 (1988).

Schoenberg, M.H., et al., "Outcome of patients with sepsis and septic shock after ICU treatment." Langenbeck's Arch. Surg. 383, 44-48, 1998.

Sexton, et al., "The use of daptomycin, a lipopeptide antibiotic, in the treatment of gram positive infections in man." Abstracts of the Interscience Conference on Antimicrobial Agents and Chemotherapy A932 (1988).

Silva, M., et al., "In vitro activity of LY146032 against gram-positive bacteria." Diagn. Microbiol. Infect. Disease 9, 79-85 (1988).

Silverman, Jared A., et al., "Resistance studies with daptomycin." Antimicrobial Agents and Chemotherapy 45(6), 1799-1802 (Jun. 2001).

Smith, K., et al., "Daptomycin versus vancomycin treatment for *Staphylococcus aureus* bacteremia ina murine model." Chemotherapy 36, 428-434 (1990).

Snydman, D.R., et al., "Comparative in vitro activities of daptomycin and vancomycin against resistant gram-positive pathogens." Antimicrobial Agents and Chemotherapy 44(12), 3447-3450 (Dec. 2000).

Stratton, et al., "Bactericidal activity of deptomycin (LY146032) compared with those of ciprofloxacin, vancomycin, and ampicillin against enterococci as determined by kill-kinetic studies." Antimicrobial Agents and Chemotherapy 31, 1014-1016 (1987).

Stratton, et al., "Effect of human serum on the bactericidal activity of daptomycin and vancomycin against staphylococcal and enterococcal isolates as determined by time-kill kinetic studies." Diagnostic Microbiology and Infectious Disease 13, 245-252 (1990).

Tally, et al., "Daptomycin: A Novel Agent for Gram-Positive Infections." Exp. Opin. Invest. Drugs 8, 1223-1238 (1999).

Tally, F.P., et al., "Daptomycin (CidecinTM) Treatment for serious gram-positive infections including endocarditis." European Congress of Clinical Microbiology and Infectious Diseases WeP233:8/1 (2000).

Tawfik, A.F., "Effects of vancomycin, teicoplanin, daptomycin and coumermycin on normal immune capabilities." J. Chemotherapy 3(4), 226-231 (1996).

Thibault, et al., "Protection against gentamicin nephrotoxicity by daptomycin in nephrectomized rats." Life Sciences 56/22, 1877-1887 (1995).

Thibault, Nathalie, et al., "Attenuation by daptomycin of gentamicin-induced experimental nephrotocity." Antimicrobial Agents and Chemotherapy 38(5), 1027-1035 (May 1994).

Thompson, "Dosage regimen design: A pharmacokinetic approach." J. Clin. Pharmacol. 32, 210-214 (1992).

Tozzi, S., et al., "Sucessful treatment of leuconostoc species bacteremia in recipients of bone marrow transplantation (BMT) by daptomycin (D)." Clin. Microbiol. Infection, Abstract and Poster, Abstract #WeP309. Clin. Microbiol Infection vol. 6, Supp. 1, 240 (May 2000).

Tripod!, Marie-Francoise, et al., "Influence of Subinhibitory Concentrations of Loracarbef (LY163892) and daptomycin (LY146032) on bacterial phagocytosis, killing and serum sensitivity." J. Antimicrobial Chemotherapy 26, 491-501 (1990).

Tym Ms, K.E., et al., "Correlation between tests of muscle involvement and clinical muscle weakness in polymyositis and dermatomyositis." Clinical Rheumatology 9(4), 523-529 (1990).

Valentine, Beth A., "Increased serum alanine aminotransferase activity associated with muscle necrosis in the dog." J. Vet. Int. Med. 4(3), 140-143, 1990.

Van Der Auwera, P., et al., "Influence of Antibiotics on Motility and Adherence of Human Neutrophils Studied in Vitro." Drugs Exptl. Clin. Res. 15(5), 211-218 (1989).

Van Der Auwera, "Ex vivo study of serum bactericidal titers and killing rates of daptomycin (LY146032) combined or not combined with amikacin compared with those of vancomycin." Antimicrob. Agents and Chemotherapy 33/10, 1783-1790, 1989.

Vance-Bryan, Kyle, et al., "Investigation of the early killing of *Stapylococcus aureus* by daptomycin by using an in vitro pharmacodynamic model." Antimicrobial Agents and Chemotherapy 36(10), 2334-2337 (Oct. 1992).

Vemuri, et al., "Enterococcal infectios: The increasing threat of nosocomial spread and drug resistance." J. Postgraduate Medicine 93, 121-128 (1993).

Verbist, L., "In vitro activity of LY146032, a new lipopeptide antibiotic, against gram-positive cocci." Antimicrobial Agents and Chemotherapy 31(2), 340-342 (Feb. 1987).

Verghese, Abraham, et al., "LY146032 in a hamster model of *Staphylococcus aureus* pneumonia: Effect on in vivo clearance and mortality and in vitro opsonophagocytic killing." Chemotherapy 34, 497-503 (1988).

Vogelman, Bennett, et al., "Kinetics of Antimicrobial Activity." J. Pediatrics 108(2), 835-840 (May 1986).

Voorn, et al., "Role of tolerance in treatment and prophylaxis of experimental *Staphylococcus areus* endocarditis with vancomycin, teicoplanin, and daptomycin." Antimicrobial Agents and Chemotherapy 38, 487-493 (1994).

(56) References Cited

OTHER PUBLICATIONS

Wantanakunakom, Chatrchai, "In-vitro activity of LY 146032, a novel cyclic lipopeptide, alone and in combination with gentamicin or tobramycin against enterococci", J. Antimicrobial Chemotherapy 19/4, 445-448 (1987).

Weinstein, Melvin P., et al., "The clinical significance of positive blood cultures in the 1990s: A prospective comprehensive evaluation of the microbiology, epidemiology, and outcome of bacteremia and fungemia in adults." Clinical Infectious Diseases 24, 584-602 (Apr. 1997).

Wheat, Lawrence J., et al., "Comparison of cefazolin, cefamandole, vancomycin, and LY146032 for prophylaxis of experimental *Staphylococcus epidermidis* endocarditis." Antimicrobial Agents and Chemotherapy 32, 63-67 (1988).

Widmer, A.F., et al., "Correlation between in vivo and in vitro efficacy of antimicrobial agents against foreign body infections." J. Infect. Dis. 162(1), 96-102 (1990).

Wood, Craig A., et al., "Influence of daptomycin on staphylococcal abscesses and experimental tobramycin nephrotoxicity." Antimicrobial Agents and Chemotherapy 33, 1280-1285 (1989).

Woodford, Neil, et al., "Current Perspectives on Glycopeptide Resistance." Clin. Mircobiol. Rev. 8, 585-615 (Oct. 1995).

Woodworth, et al., "Single-Dose Pharmacokinetics and Antibacterial Activity of Daptomycin, a New Lipopeptide Antibiotic, in Healthy Volunteers." Antimicrobial Agents and Chemotherapy 36, 318-325 (1992).

Woodworth, et al., "Tobramycin and Daptomycin Disposition when Co-Administered to Healthy Volunteers." J. Antimicrobial Chemotherapy 33, 655-659 (1994).

Zamora, S., et al., "Elevated aminotransferase activity as an indication of muscular dystrophy: Case reports and review of the literature." Clinical Gastroenterology 10(6), 389-393 (Oct. 1996).

Bayer, Arnold S. et al. LY146032 compared with penicillin G in experimental aortic valve endocarditis caused by Group G Streptococci. Antimicrobial Agents and Chemotherapy 32, 141-143 (1988).

Jacobus, N.V. et al. Effect of daptomycin on fecal suspensions seeded with a vancomycin-resistant *Enterococcus*. Interscience Conference on Antimicrobial Agents and Chemotherapy, Poster #F-113 (1998).

Dvorchik, B, et al., "Daptomycin Pharmacokinetics and Safety following Administration of Escalating Doses Once Daily to Healthy Subjects," Antimicrobial Agents and Chemotherapy vol. 47, No. 4, Apr. 2003, pp. 1318-1323.

Leclercq, et al., "Effects of Combinations of 6-Lactams, Daptomycin, Gentamicin, and Glycopeptides against Glycopeptide-Resistant Enterococci", Antimicrob. Agents Chemother. 35 (1), 92-98 (1991).

Lee, et al., "Daptomycin versus conventional therapy in the treatment of endocarditis and bacteremia." Abstracts of the Interscience Conference on Antimicrobial Agents and Chemotherapy A885 (1991).

Dougherty, Steven H., et al., "Impact of LY146032 on *Streptococcus (Enterococcus) faecalis* translocation in mice." Antimicrobial Agents and Chemotherapy 32, 337-340 (1988).

Draper, Ruth P., "Studies on the muscle toxicant 2,3,5,6-tetramethyl P-phenylenediamine: Effects on various biomarkers including urinary creatine and taurine." Arch. Toxicol. 69, 111-117 (1994).

Drusano, George L., et al., "Pharmacodynamics of a fluoroquinolone antimicrobial agent in a neutropenic rat model of pseudomonas sepsis." Antimicrobial Agents and Chemotherapy 37(3), 483-490 (Mar. 1993).

Duh, Ruay-Wang, et al., "In vitro activity of 19 antimicrobial agents against enterococci from healty subjects and hospitalized patients and use of an ace gene probe from *Enterococcus faecalis* for species identification." Microbial Drug Resistance 7(1), 39-46 (2001).

Duska, F., et al., "The pyrophosphate heart scintigram in children with progressive muscular dystrophy." Nucl. Med. 23, 189-191 (1984).

Ehlers, S. et al., "Influence of LY146032 (daptomycin) on the cell-mediated immunity." (Confidential Communication).

Eliopoulos, George M., et al., "In vitro activity and mechanism of action of A21978C1, a novel cyclic lipopeptide antibiotic." Antimicrobial Agents and Chemotherapy 27(3), 357-362 (Mar. 1985).

El-Mady, Abdelhady, et al., "The bactericidal activity of ampicillin, daptomycin, and vancomycin against ampicillin-resistant *Enterococcus faecium*." Diagn. Microbiol. Infect. Dis. 14, 141-145 (1991).

Etienne, et al., "A phase I, double-blind, placebo-controlled study of the tolerance and pharmacokinetic behaviour or RP 59500." J. Antimicrobial. Chemotherapy 30/Supp. A, 123-131 (1992), STN online, file EMBASE, Abstract.

Fasching, C.E., et al., "Treatment evaluation of experimental staphylococcal infections: Comparison of Beta-lactam, lipopeptide, and glycopeptide antimicrobial therapy." J. Lab. Clin. Med. 116(5), 697-706 (1990).

Fass, Robert J., et al., "In vitro activity of LY146032 against staphylococci, and enterococci." Antimicrobial Agents and Chemotherapy 30(5), 781-784 (Nov. 1986).

Fischer, W., "Physiology of Lipoteichoic Acids in Bacteria." Adv. Microbial Physiol. 29, 234-303, 1988.

Flandrois, et al., "Early Stages of In Vitro Killing Curve of LY146032 and Vancomycin for *Staphylococcus aureus*." Antimicrobial Agents and Chemotherapy 32, 2611-2616 (1992).

Fontana, Roberta, et al., "In vitro response to bactericidal activity of cell wall-active antibiotics does not support the general opinion that enterococci are naturally tolerant to these antibiotics." Antimicrobial Agents and Chemotherapy 34(8), 1518-1522 (Aug. 1990).

Fowler, et al., "Daptomycin versus standard therapy for Bacteremia and Endocarditis" by *Staphylococcus aureus*355:653-65, 2006.

Freeman, Collin D., et al., "Once-daily dosing of aminoglycosides: Review and recommendation for clinical practice." J. Antimicrobial Chemotherapy 39, 677-686 (1997).

Freireich, et al., "Quantitative Comparison of Toxicity of Anticancer Agents in Mouse, Rat, Hamster, Dog, Monkey and Man." Cancer Chemotherapy Reports 50, 219-244 (1966).

Fuchs, P.C., et al., "Daptomycin susceptibility tests: Interpretive criteria, quality control, and effect of calcium on in vitro tests." Diagnostic Microbiology and Infectious Disease 38, 51-58 (2000).

Fuchs, P.C., et al., "Daptomycin susceptibility tests: Provisional criteria, quality control, and importance of Ca++ concentration in test media." Interscience Conference on Antimicrobial Agents and Chemotherapy Poster #350 (1999).

Garrison, et al., "Assessment of effects of protein binding or daptomycin and vancomycin killing of *Staphylococcus aureus* by using an in vitro phamacodynamic model." Antimicrobial Agents and Chemotherapy 34, 1925-1931 (1990).

Garrison, et al., "Suboptimal Effect of Daptomycin in the Treatment of Bacteremias." Southern Medical Journal 82: 1414-1415, 1989.

Golan, Y. et al., "Daptomycin for line-related leuconostoc bacteraemia." J. Antimicrobial Chemotherapy 47, 357-368 (2001).

Goldstein, E.J.C. et al., "In vitro activity of daptomycin (CidecinTM), Quinupristin/Dalfopristin, linezolid and vancomycin against 275 gram-positive aerobic and anaerobic organisms." Interscience Conference on Antimicrobial Agents and Chemotherapy Poster #2293 (2000).

Gorbach, Sherwood L. et al., "Treatment of Infectious Diseases." Infectious Diseases 2d ed., 176, 190 (1998).

Gray, et al., "Antibiotic-resistant enterococci." J. Hospital Infection 21, 1-14—(1992).

Griswold, et al., "Quinupristin-dalfopristin (RP 59500): An injectable streptogramin combination." American J. Health-System Pharmacy 53/17, 2045-2053 (1996), STN online, file EMBASE, Abstract.

Hanberger, et al., "Pharmacodynamics of Daptomycin and Vancomycin on *Enterococcus faecalis* and *Staphylococcus aureus* Demonstrated by Studies of Initial Killing and Postantibiotic Effect and Influence of Ca2+ and Albumin on these Drugs." Antimicrobial Agents and Chemotherapy 35, 1710-1716 (1991).

Hanberger, Hakan "Pharmacodynamic effects of antibiotics—Studies on bacterial morphology, initial killing, postantibiotic effect and effective regrowth time." Linkoping University Medical Dissertations No. 357 (1992).

Haworth, Charles S., et al., "*Staphylococcus aureus* ventriculitis treated with single-soe intraventricular vancomycin or daptomycin

(56) References Cited

OTHER PUBLICATIONS (LY146032): Bacterial and antibiotic kinetics in hydrocephalic rabbits." Antimicrobial Agents and Chemotherapy 34, 245-251 (1990).

Heine, H.S., et al., "In vitro activity of daptomycin, spariloxacin, quinupristin-dalfopristin and other antibiotics against *Bacillus anthracis* strains." Interscience Conference on Antimicrobial Agents and Chemotherapy Poster #517 (2000).

Herscovici, Lisette, et al., "Efficacy and safety of once daily versus intermittent dosing of tobramycin in rabbits with acute pyelonephritis." Scand J. Infect. Dis. 20, 205-212 (1988).

Hindes, R.G., et al., "Treatment of experimental endocarditis caused by a beta-lactamase-producing strain of *Enterococcus faecalis* with high-level resistance to gentamicin." Antimicrobial Agents and Chemotherapy 33, 1019-1022 (1989).

Hiramatsu, K., "Reduced susceptibility of *Staphylococcus aureus* to vancomycin." MMWR 46, 624-626 (Jul. 11, 1997).

Hyatt, Judith M., et al., "The importance of phamacokinetic/pharmacodynamic surrogate markers to outcome: Focus on antibacterial agents." Clin. Pharmacokinetic Concepts 28(2), 143-160 (1995).

International Search Report for PCT/US01/49167, mailed Feb. 20, 2003.

Jacobus, N.V., et al., "In vitro activity of daptomycin against resistant gram-positive pathogens." Interscience Conference on Antimicrobial Agents and Chemotherapy Abstract F-112 (1998).

Jones, Ronald N., et al., "Antimicrobial activity and spectrum of LY146032, a lipopeptide antibiotic, including susceptibility testing recommendations." Antimicrobial Agents and Chemotherapy 31(4), 625-629 (1987).

Jones, Ronald N., et al., "Changing patterns of infection: A global picture." 8th International Congress on Infectious Diseases 200-209 (May 16, 1998).

Kaatz, et al., "Daptomycin Compared with Teicoplanin and Vancomycin for Therapy of Experimental *Staphylococcus aureus* Endocarditis." Antimicrobial Agents and Chemotherapy 34, 2081-2085 (1990).

Kaatz, G.W., et al., "Development of daptomycin resistance (D') in Experimental *Staphylococcus aureus* (SA) endocarditis." 33rd Interscience Conference on Antimicrobial Agents and Chemotherapy Abstract #155 (1993).

Katz, D.E., et al., "A pilot study of high-dose short duration daptomycin for the treatment of patients with complicated skin and skin structure infections caused by gram-positive bacteria," Intl. J. Clin. Practice 2008.

Kennedy, et al., "Daptomycin (LY146032) for prevention and treatment of experimental aortic valve endocarditis in rabbits." Antimicrobial Agents and Chemotherapy 33(9), 1522-1525 (1989).

Kephart, Phyllis A., et al., "Comparison of the investigational drug, LY146032 with vancomycin in experimental pneumonia due to methicillin-resistant *Staphylococcus aureus*." J. Antimicrobial Chemotherapy 21, 33-39 (1988).

King, Charles H.. et al.. "Pharmacokinetics of tobramycin and gentamicin in abusers of intravenous drugs." Antimicrobial Agents and Chemotherapy 27(3), 285-290 (Mar. 1985).

Kirsch, Lee E., et al., "Kinetics of the aspartyl tranpeptidation of daptomycin, a novel lipopeptide antibiotic." Pharmaceutical Res. 6(5), 387-393 (1989).

Kreft, B., et al., "Experimental studies on nephrotoxicity and pharmacokinetics of LY146032 (daptomycin) in rats." J. Antimicrobial Chemotherapy 25, 635-643 (1990).

Kuechle, David K., et al. "Elution of vancomycin, daptomycin, and amikacin from acrylic bone cement." Clin. Orthopedics and Related Research 264, 302-308 (1991).

Lakey, Jeremy H., et al., "Fluorescence indicates a calcium-dependent interaction between the lipopeptide antibiotic LY146032 and phospholipid membranes." Biochemistry 4641-4645 (1988).

Lamp, et al., "In vitro pharmacodynamic effects of concentration, pH, and growth phase on serum bactericidal activities of daptomycin and vancomycin." Antimicrobial Agents and Chemotherapy 36, 2709-2714 (1992).

Eliopoulos, George M. et al. In vitro and in vivo activity of LY146032, a new cyclic lipopeptide antibiotic. Antimicrobial Agents and Chemotherapy 30, 532-535 (1986).

METHODS FOR PREPARING PURIFIED LIPOPEPTIDES

CROSS-REFERENCE TO RELATED APPLICATIONS

The present application is a continuation of U.S. application Ser. No. 11/108,380, filed Apr. 18, 2005; which is a continuation-in-part application of U.S. patent application Ser. No. 10/023,517, filed Dec. 17, 2001, which claims the benefit of U.S. Provisional Application No. 60/256,268, filed Dec. 18, 2000; Ser. No. 60/274,741, filed Mar. 9, 2001; Ser. No. 60/341,315, filed Dec. 13, 2001; and Ser. No. 60/340,525, filed Dec. 13, 2001. U.S. application Ser. No. 11/108,380 is also a continuation-in-part of U.S. patent application Ser. No. 10/024,701, filed Dec. 17, 2001, which claims the benefit of U.S. Provisional Application No. 60/256,268, filed Dec. 18, 2000; Ser. No. 60/274,741, filed Mar. 9, 2001; Ser. No. 60/341,315, filed Dec. 13, 2001; and Ser. No. 60/340,525, filed Dec. 13, 2001. U.S. application Ser. No. 11/108,380 is also a continuation-in-part of U.S. patent application Ser. No. 10/024,405, filed Dec. 18, 2001, which claims the benefit of U.S. Provisional Application No. 60/256,268, filed Dec. 18, 2000 and Ser. No. 60/274,741, filed Mar. 9, 2001. The contents of each of the above-referenced applications are incorporated herein by reference in their entireties.

TECHNICAL FIELD OF THE INVENTION

The present invention relates to crystalline and crystalline-like forms of lipopeptides, including daptomycin, a lipopeptide antibiotic with potent bactericidal activity against gram-positive bacteria, including strains that are resistant to conventional antibiotics. The present invention also relates to processes for preparing crystalline or crystal-like forms of the lipopeptide and to methods of purifying lipopeptides including daptomycin. The present invention also relates to pharmaceutical compositions comprising the purified form of the lipopeptide and methods of using these compositions.

BACKGROUND OF THE INVENTION

The rapid increase in the incidence of gram-positive infections—including those caused by antibiotic-resistant bacteria—has sparked renewed interest in the development of novel classes of antibiotics. One such class is the lipopeptide antibiotics, which includes daptomycin. Daptomycin has potent bactericidal activity in vitro against clinically relevant gram-positive bacteria that cause serious and life-threatening diseases. These bacteria include, but are not limited to, resistant pathogens, such as vancomycin-resistant enterococci (VRE), methicillin-resistant *Staphylococcus aureus* (MRSA), glycopeptide intermediary susceptible *Staphylococcus aureus* (GISA), coagulase-negative staphylococci (CNS), and penicillin-resistant *Streptococcus pneumoniae* (PRSP), for which there are very few therapeutic alternatives. See, e.g., Tally et al., 1999, *Exp. Opin. Invest. Drugs* 8:1223-1238. Daptomycin's inhibitory effect is a rapid, concentration-dependent bactericidal effect in vitro and in vivo, and a relatively prolonged concentration-dependent post-antibiotic effect in vivo.

Daptomycin is described by Baltz in *Biotechnology of Antibiotics, 2nd Ed.*, ed. W. R. Strohl (New York: Marcel Dekker, Inc.), 1997, pp. 415-435. Daptomycin, also known as LY 146032, is a cyclic lipopeptide antibiotic that can be derived from the fermentation of *Streptomyces roseosporus*. Daptomycin is a member of the factor A-21978$C_0$ type antibiotics of *S. roseosporus* and is comprised of a decanoyl side chain linked to the N-terminal tryptophan of a cyclic 13-amino acid peptide (FIG. 1). Daptomycin has an excellent profile of activity because it is highly effective against most gram-positive bacteria; it is highly bactericidal and fast-acting; it has a low resistance rate and is effective against antibiotic-resistant organisms. The compound is currently being developed in a variety of formulations to treat serious infections caused by bacteria, including, but not limited to, methicillin-resistant *Staphylococcus aureus* (MRSA) and vancomycin-resistant enterococci (VRE).

A number of United States patents describe A-21978$C_0$ antibiotics and daptomycin-related lipopeptides including daptomycin (LY 146032). These patents also describe methods of producing and isolating the A-21978$C_0$ antibiotics and daptomycin-related lipopeptides.

U.S. Pat. Nos. RE32,333, RE32,455, 4,800,157, 4,874, 843, and 4,885,243 describe methods of synthesizing and isolating daptomycin from fermentation cultures of *Streptomyces roseosporus*. U.S. Pat. Nos. RE32,310, RE32,311, 4,537,717, 4,482,487 and 4,524,135 describe A-21978$C_0$ antibiotics and methods of deacylating the A-21978$C_0$ antibiotic and reacylating the peptide nucleus and antibiotic derivatives made by this process. U.S. Pat. No. 5,912,226 (hereafter the '226 patent) describes the identification and isolation of two impurities produced during the manufacture of daptomycin, anhydro-daptomycin and the β-isomer form of daptomycin. None of these United States patents discloses a method for precipitating or crystallizing a lipopeptide in a manner to increase purity of the lipopeptide.

U.S. Pat. No. 4,439,425 (hereafter the '425 patent) discloses a crystalline lipopeptide and a method of crystallizing the lipopeptide. The lipopeptide disclosed in the '425 patent is structurally dissimilar from daptomycin and daptomycin-related lipopeptides. U.S. Pat. No. 5,336,756 (hereafter the '756 patent) also discloses a crystalline cyclic lipopeptide comprising a hexapeptide. The crystalline cyclic lipopeptide disclosed in the '756 patent is also structurally dissimilar from daptomycin and daptomycin-related lipopeptides. The '756 patent discloses that the lipopeptide, an echinocandin-type compound, can be obtained when aqueous n-propanol is employed as the crystallizing solvent. See, e.g., cols. 1-2 of the '756 patent. Neither the '425 patent nor the '756 patent disclose methods of crystallizing or precipitating daptomycin or a daptomycin-related lipopeptide, nor do they disclose methods of crystallizing or precipitating lipopeptides produced by *Streptomyces*.

It would be advantageous to develop a method of crystallizing or precipitating daptomycin and daptomycin-related lipopeptides to provide an improved purification method for these lipopeptides. In addition, a crystalline or highly purified precipitated form of daptomycin or other daptomycin-related lipopeptide would be useful in formulating pharmaceutical compositions for treating bacterial infections. Further, a crystalline or highly purified precipitated form of daptomycin or daptomycin-related lipopeptide would be useful in a method to make a sterile product, particularly bulk sterile product. Thus, there is a need for methods to produce crystalline or precipitated daptomycin and daptomycin-related lipopeptides and the crystalline or precipitated forms of the lipopeptides produced thereby. However, there has been no simple and robust method that has been effective in crystallizing or precipitating daptomycin or a daptomycin-related lipopeptide that results in a lipopeptide that is more pure after crystallization or precipitation than before.

SUMMARY OF THE INVENTION

The instant invention addresses these problems by providing crystalline and crystalline-like forms of lipopeptides, particularly daptomycin and daptomycin-related lipopeptides and methods for producing them. In one embodiment, the invention provides methods for crystallizing lipopeptides. In another embodiment, the methods provide a lipopeptide that is more pure after crystallization or precipitation than before crystallization or precipitation.

The invention also provides robust processes for producing and purifying lipopeptides comprising, inter alia, crystallizing or precipitating lipopeptides. In one embodiment, the crystallizing or precipitating steps of the processes are used to purify the lipopeptides. In another embodiment, the processes are used for large-scale and/or commercial production of lipopeptides, preferably daptomycin.

The invention further provides highly purified crystalline or crystal-like forms of daptomycin and daptomycin-related lipopeptides. In one embodiment, the crystalline or crystal-like forms of the lipopeptides may be used in pharmaceutical compositions. In another embodiment, the invention comprises methods of using the pharmaceutical compositions.

DETAILED DESCRIPTION OF THE INVENTION

Objects of the Invention

Figure 1:
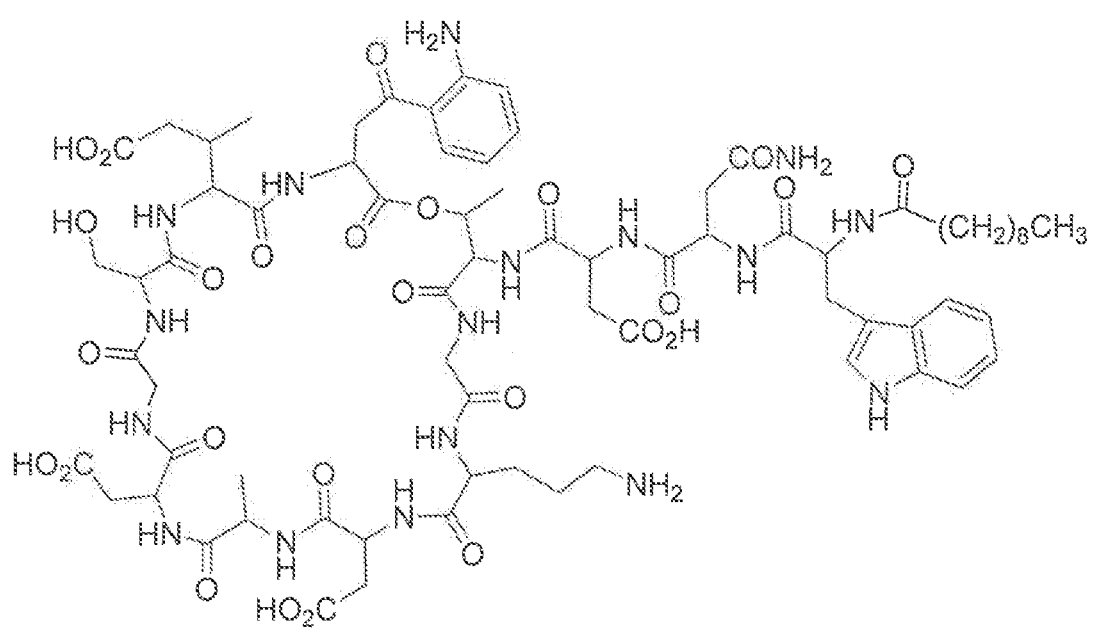
FIG. 1 shows the structure of daptomycin.

One object of the present invention is to provide methods for crystallizing or precipitating lipopeptides. In one embodiment, the methods are used to crystallize or precipitate daptomycin or a daptomycin-related lipopeptide. In another embodiment, the methods increase the purity of the lipopeptide compared to the purity of the lipopeptide prior to crystallization or precipitation. The methods comprise the steps of providing an amorphous preparation of a lipopeptide and crystallizing or precipitating the lipopeptide under conditions in which the crystalline or precipitated, crystal-like lipopeptide is more pure than the amorphous preparation of the lipopeptide. In one embodiment, the amorphous preparation is no greater than 92% pure and the crystalline or crystal-like lipopeptide purified therefrom is at least 95% pure, and may be at least 96%, 97% or 98% or more pure. In another embodiment, the amorphous preparation is no greater than 80% pure and the crystalline or crystal-like lipopeptide purified therefrom is at least 95% pure, and may be at least 96%, 97% or 98% or more pure. In another embodiment, the amorphous preparation is no greater than 60% pure and the crystalline or crystal-like lipopeptide purified therefrom is at least 95% pure, and may be at least 96%, 97% or 98% ore more pure. In yet another embodiment, the amorphous preparation is no greater than 40% pure and the crystalline or crystal-like lipopeptide purified therefrom is at least 95% pure, and may be at least 96%, 97% or 98% or more pure. In another embodiment, the amorphous preparation is no greater than 20% pure and the crystalline or crystal-like lipopeptide purified therefrom is at least 95% pure, and may be at least 96%, 97% or 98% or more pure. In a further preferred embodiment, the amorphous preparation is no greater than 10% pure and the crystalline or crystal-like lipopeptide purified therefrom is at least 95% pure, and may be at least 96%, 97% or 98% or more pure.

Another object of the invention is to provide processes for making and purifying a lipopeptide comprising, inter alia, crystallizing or precipitating the lipopeptides. In one embodiment, the crystallizing or precipitating steps are used to purify the lipopeptides. In a preferred embodiment, the crystallization or precipitation is performed by batch crystallized or precipitation. In another embodiment, the process is a large-scale process for commercial production of a lipopeptide, preferably daptomycin or a daptomycin-related lipopeptide. In one embodiment, the lipopeptide is produced by fermentation. The fermentation product is then purified by a variety of purification techniques including crystallization or precipitation. In one embodiment, the crystallization or precipitation step may be used in combination with other purification techniques including microfiltration, size exclusion ultrafiltration and/or anion exchange chromatography. In one embodiment, the crystallization or precipitation step is used to replace one or more purification techniques that is used in a purification process that does not use crystallization or precipitation. In another embodiment, the crystallization or precipitation step is used to increase purification compared to the other steps without the crystallization or precipitation step. In a preferred embodiment, the method comprises a step of collecting the crystalline or crystal-like lipopeptide after crystallization or precipitation.

Figure 2:
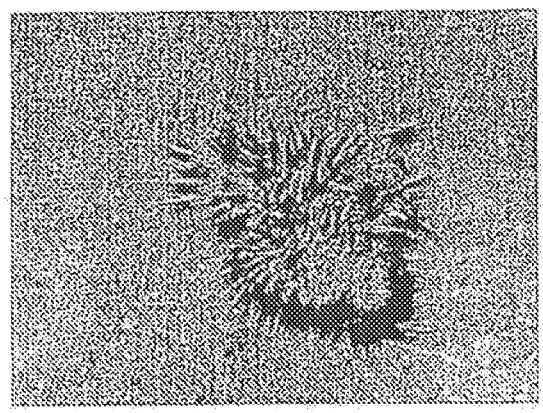
FIG. 2 shows a photomicrograph of urchin-like crystal or crystal-like particle of daptomycin produced by the method described in Example 12.

Another object of the present invention is to provide highly purified, e.g. sterile, crystalline or crystal-like forms of lipopeptides. In one embodiment, the lipopeptides are daptomycin or a daptomycin-related lipopeptide. The crystalline or crystal-like form of the lipopeptide may have any crystalline or crystal-like shape including urchin-like (cluster of needles joined together to visually resemble a sea urchin) (see FIG. 2), needle-like (see FIG. 3), rod-like (see FIG. 4), plate-like or flake-like. In one embodiment, the crystalline or crystal-like lipopeptide has a purity of at least 80%, and may be at least 85%, 90% pure. In another embodiment, the crystalline or crystal-like form of the lipopeptide has a purity of at least 95%, and may be at least 96%, 97%, 98% pure or more.

A further object of the present invention is to provide a pharmaceutical composition comprising a crystalline or crystal-like form of a lipopeptide. In one embodiment, the lipopeptide is daptomycin or a daptomycin-related lipopeptide. In one embodiment, the pharmaceutical comp. is enterically coated for oral administration or is formulated in the form of micronized particles or microspheres. In other embodiments, the invention provides methods for administering the pharmaceutical compositions to subjects in need thereof.

DEFINITIONS

Unless otherwise defined, all technical and scientific terms used herein have the meaning as commonly understood by one of ordinary skill in the art to which this invention belongs. The practice of the present invention employs, unless otherwise indicated, conventional techniques of chemistry, biochemistry, biophysics and microbiology and basic terminology used therein.

The term "lipopeptide" refers to a molecule that comprises a lipid-like moiety covalently linked to a peptide moiety, as well as salts, esters, amides and ethers thereof. The term "lipopeptide" also encompasses protected forms of lipopeptides in which one or more amino, carboxylate or hydroxyl groups are protected. See, e.g., "Protective Groups in Organic Synthesis" by Theodora W. Greene, John Wiley and Sons, New York, 1981 for examples of protecting groups. In one embodiment, the lipopeptide is an antibiotic. In another embodiment, the lipopeptide is LY 303366, echinocandins, pneumocandins, aculeacins, viscosin, surfactin, plipastatin B1, amphomycin or the lipopeptide derivative disclosed in U.S. Pat. No. 5,629,288. These lipopeptides are known in the art. See, e.g., U.S. Pat. No. 5,202,309 and International PCT Application WO 00/08197. In another embodiment, the lipopeptide is a daptomycin-related molecule. In another embodiment, the lipopeptide is daptomycin.

A "daptomycin-related molecule" includes, inter alia, daptomycin, A54145 or other lipopeptide that is structurally related to daptomycin, such as a daptomycin-related lipopeptide, including all stereoisomers that may be made at any chiral centers present in these molecules.

A "daptomycin-related lipopeptide" includes, without limitation, a lipopeptide disclosed in U.S. Pat. Nos. 4,537,717, 4,482,487, RE32,311, RE32,310, and 5,912,226, currently in reissue as U.S. application Ser. No. 09/547,357. Daptomycin-related lipopeptides also include those disclosed in International PCT Publication WO 01/44272, published Jun. 21, 2001; International PCT Publication WO 01/44274, published Jun. 21, 2001; and International PCT Publication WO 01/44271, published Jun. 21, 2001; all of these applications are specifically incorporated herein by reference. The daptomycin-related lipopeptides disclosed in the above-identified applications relate to synthetic and semisynthetic lipopeptides in which the ornithine and/or kynurine residues, and/or the fatty acid side chain of daptomycin, are modified. Daptomycin-related lipopeptides further include an $A-21978C_0$ antibiotic in which the n-decanoyl fatty acid side chain of daptomycin is replaced by a n-octanoyl, n-nonanoyl, n-undecanoyl, n-dodecanoyl, n-tridecanoyl or n-tetradecanoyl fatty acid side chain.

The term "daptomycin" refers to the n-decanoyl derivative of the factor $A-21978C_0$-type antibiotic that contains an α-aspartyl group. "Daptomycin" is synonymous with LY 146032.

The term "anhydro-daptomycin" refers to a daptomycin-related lipopeptide in which an α-aspartyl group of daptomycin is cyclized to a succinimido group. See, e.g., the '226 patent for the structure of anhydro-daptomycin.

The term "β-isomer" or "β-isomer of daptomycin" refers to a daptomycin-related lipopeptide that contains a β-aspartyl group instead of an α-aspartyl group. See, e.g., the '226 patent for the structure of β-isomer of daptomycin.

The term "isolated" refers to a compound or product that is at least 5%, 10%, 20%, 30%, 40%, 50%, 60%, 70%, 80% or 90% of the compound present in a mixture. It will be understood that the term "isolated" also refers to a compound that is at least 5-10%, 10-20%, 20-30%, 30-40%, 40-50%, 50-60%, 60-70%, 70-80% or 80-90% of the compound present in the mixture group. The percentage of compound in a mixture may be measured by any means known in the art, as described below for measuring purity of a compound.

"Substantially pure" refers to a sample having at least 95% of a desired compound. Preferably, daptomycin is "substantially pure" when at least 95% to at least 97% of a sample is daptomycin. Similarly, a daptomycin-related lipopeptide, is "substantially pure" when at least 95% to at least 97% of a sample is a daptomycin-related lipopeptide.

Daptomycin or a daptomycin-related lipopeptide is "essentially pure" when at least 98% to at least 99% of a sample is daptomycin or a daptomycin-related lipopeptide, respectively.

Daptomycin or a daptomycin-related lipopeptide is "substantially free" of another compound when the other compound is present in an amount that is no more than 1% of the amount of the daptomycin or the daptomycin-related lipopeptide preparation, respectively.

Daptomycin or a daptomycin-related lipopeptide is "essentially free" of another compound when the other compound is present in an amount that is no more than 0.5% of the amount of the daptomycin or the daptomycin-related lipopeptide preparation, respectively.

Daptomycin or a daptomycin-related lipopeptide is "free" of another compound when the other compound is present in an amount that is no more than 0.1% of the amount of the daptomycin or the daptomycin-related lipopeptide preparation, respectively. Alternatively, daptomycin or a daptomycin-related lipopeptide is "free" of another compound when the compound cannot be detected by HPLC under conditions of maximum sensitivity in which a limit of detection is approximately 0.05% or less of the amount of the daptomycin or the daptomycin-related lipopeptide preparation, respectively.

"Purified" daptomycin refers to substantially pure daptomycin, essentially pure daptomycin, or a salt thereof, or to daptomycin or a salt thereof which is substantially free, essentially free, or free of another compound. Similarly, a "purified" daptomycin-related lipopeptide refers to a substantially pure daptomycin-related lipopeptide, an essentially pure daptomycin-related lipopeptide, or a salt thereof, or to a daptomycin-related lipopeptide or a salt thereof which is substantially free, essentially free, or free of another compound.

"Crude" daptomycin refers to daptomycin or a salt thereof that is less than 90% pure. Similarly, "crude" daptomycin-related lipopeptide refers to a daptomycin-related lipopeptide or a salt thereof that is less than 90% pure.

"Semi-purified" daptomycin refers to daptomycin or a salt thereof that is at least 90% pure and less than 95% pure. Similarly, "semi-purified" daptomycin-related lipopeptide refers to a daptomycin-related lipopeptide or a salt thereof that is at least 90% pure and less than 95% pure.

The purity of daptomycin, daptomycin-related lipopeptide or of another lipopeptide refers to the lipopeptide prior to its formulation in a pharmaceutical composition. The purity of the lipopeptide is referred to by "percent purity." The measure of purity is not a measure of degree of crystallinity of the crystalline preparation. The purity may be measured by any means including nuclear magnetic resonance (NMR), gas chromatography/mass spectroscopy (GC/MS), liquid chromatography/mass spectroscopy (LC/MS) or microbiological assays. One preferred means for measuring the purity of daptomycin is by analytical high pressure liquid chromatography (HPLC). Two methods of analytical HPLC are described in International PCT Publication WO 01/53330, published Jul. 26, 2001, which is herein incorporated specifically by reference.

A "lipopeptide crystal" refers to one or more crystals of a lipopeptide or of a lipopeptide salt. The determination of a lipopeptide as a crystal can be determined by any means including, inter alia, optical microscopy, electron microscopy, x-ray powder diffraction, solid state nuclear magnetic resonance (NMR) or polarizing microscopy. Microscopy can be used to determine the crystal length, diameter, width, size and shape, as well as whether the crystal exists as a single particle or is polycrystalline.

A lipopeptide or lipopeptide particle is "crystal-like" if it is determined to have crystalline characteristics when determined by one means, e.g., visually or by optical or polarizing microscopy, but does not have crystalline characteristics when determined by another means, e.g., x-ray powder diffraction. A lipopeptide that is "crystal-like" may be crystalline under certain conditions but may become non-crystalline when subjected to other conditions.

A "crystalline lipopeptide" or a "crystalline form of a lipopeptide" refers to a preparation of a lipopeptide or salt thereof that comprises lipopeptide crystals. In one embodiment, a crystalline lipopeptide may comprise some amount of amorphous lipopeptide. In one embodiment, the crystalline lipopeptide comprises more than 50% by weight of lipopeptide crystals. In another embodiment, the crystalline lipopeptide comprises more than 60%, 70%, 80%, 90% or 95% of lipopeptide crystals. The crystalline lipopeptide may comprise 50-60%, 60-70%, 70-80%, 80-90% or 90-95% of lipopeptide crystals. In another embodiment, the crystalline lipopeptide comprises more than 95% of lipopeptide crystals, e.g., at least 96%, 97%, 98% or 99% lipopeptide crystals or 100% lipopeptide crystals. The crystalline lipopeptide may also comprise anywhere from 95-100% lipopeptide crystals. The percent by weight of lipopeptide crystals refers to the lipopeptide preparation prior to its formulation in a pharmaceutical composition.

An "amorphous" form of a lipopeptide refers to a lipopeptide preparation that comprises few or no lipopeptide crystals or crystal-like lipopeptides (or crystal-like particles) as defined herein. In one embodiment, an amorphous lipopeptide comprises less than 20% by weight of lipopeptide crystals or crystal-like lipopeptides. In another embodiment, an amorphous lipopeptide comprises less than 10% by weight of lipopeptide crystals or crystal-like lipopeptides. In another embodiment, an amorphous lipopeptide comprises less than 5% by weight of lipopeptide crystals or crystal-like lipopeptides. In a still further preferred embodiment, an amorphous lipopeptide comprises less than 1% by weight of lipopeptide crystals or crystal-like lipopeptides.

"Batch crystallization" refers to a method in which the lipopeptide of interest is mixed with the crystallization reagents in solution and the lipopeptide is allowed to crystallize in solution. "Batch precipitation" refers to a method in which the lipopeptide is mixed with precipitation reagents in solution and the lipopeptide is allowed to precipitate in solution. In one embodiment, the crystalline or precipitated preparation is collected from the solution. In another embodiment, the crystalline or precipitated preparation is collected by filtration or centrifugation.

"Organic precipitant" refers to a polyethylene glycol (PEG) or polyethylene glycol monomethyl ether (PEG MME) or compounds that are chemically similar.

"Salts" refer to ionic compounds. These ionic compounds may act as precipitants.

"Low molecular weight alcohols" are organic compounds containing at least one alcohol functional group, and eight carbon atoms or less. For example, low molecular weight alcohols include, without limitation, methanol, isopropanol, and tert-butanol.

"Polyhydric alcohols" refer to compounds that contain more than one alcohol group, and less than eight carbon atoms. Polyhydric alcohols, for example, include, without limitation, 1,6 hexanediol, ethylene glycol, propylene glycol, glycerol, 1,2-propanediol, 2-methyl-2,4-pentanediol and 1,4 butanediol.

"Container" refers to a receptacle for holding goods. For example, a container may include, without limitation, an ampule, vial, tube, bottle, or cylinder.

Methods for Producing Purified Lipopeptides

One object of the invention is to provide a method for purifying a lipopeptide comprising the steps of providing an amorphous preparation of a lipopeptide and crystallizing or precipitating the lipopeptide. In one embodiment, the lipopeptide has a higher degree of purity after crystallization or precipitation than prior to being subjected to crystallization or precipitation. Lipopeptides may be crystallized by hanging drop, sitting drop or sandwich drop vapor diffusion, liquid-liquid or free interface diffusion, microdialysis or dialysis, slow solvent evaporation, sublimation, or microbatch or batch crystallization. In general, a lipopeptide may be precipitated in a similar way, preferably a lipopeptide is precipitated by batch precipitation. In a preferred embodiment, the crystallized or precipitated lipopeptide is daptomycin or a daptomycin-related lipopeptide. In a more preferred embodiment, the crystallized or precipitated lipopeptide is daptomycin.

Lipopeptides may be crystallized or precipitated following the teachings of this specification. In one embodiment, a lipopeptide can be crystallized or precipitated by providing a solution comprising a lipopeptide with a low molecular weight or polyhydric alcohol, a pH buffering agent and a salt comprising a monovalent or divalent cation and allowing precipitation or crystallization to occur, as discussed further infra. In another embodiment, the salt has buffering capacity such that an additional pH buffering agent does not have to be present in the solution. In another embodiment, the salt comprises a divalent cation. In a preferred embodiment, the solution provided does not include PEG or PEG-MME or chemically similar compounds. In an embodiment, the method for precipitating or crystallizing the lipopeptide generally comprises the steps of:

a) mixing the lipopeptide with a salt comprising a monovalent or divalent cation, an optional pH buffering agent and a low molecular weight or polyhydric alcohol; and b) allowing the lipopeptides to precipitate or crystallize from the solution under the appropriate temperature conditions.

The samples may be monitored, inter alia, for crystal or precipitate formation by microscopic examination and the yield may be followed spectrophotometrically. In a preferred embodiment, the crystallized or precipitated lipopeptide is daptomycin or a daptomycin-related lipopeptide.

In another embodiment, the lipopeptide can be crystallized by providing a solution comprising a low molecular weight or polyhydric alcohol(s), salts and an organic precipitant as discussed further infra. In a more preferred embodiment, the crystallized lipopeptide is daptomycin. In general, for batch crystallization, the lipopeptide is dissolved in a solution and low molecular weight alcohols, salts, buffers and/or organic precipitants are added to the solution. The samples are then crystallized under the appropriate temperature conditions, with or without stirring. The samples may be monitored, inter alia, for crystal formation by microscopic examination and the yield may be followed spectrophotometrically.

As discussed above, the lipopeptide, preferably daptomycin or a daptomycin-related lipopeptide, is crystallized or precipitated in the presence of one or more alcohols. In a preferred embodiment, the alcohol is a low molecular weight or polyhydric alcohol. Examples of low molecular weight or polyhydric alcohols include, without limitation, methanol, isopropanol, tert-butanol, 1,6 hexanediol, ethylene glycol, propylene glycol, glycerol, 1,2-propanediol, 2-methyl-2,4-pentanediol and 1,4 butanediol. In a preferred embodiment, the alcohol is isopropanol, tert-butanol, glycerol, 1,6-hexanediol, 1,2-propanediol, 1,4-butanediol, propylene glycol and/or ethylene glycol. In a more preferred embodiment, the alcohol is isopropanol.

Salts include, inter alia, magnesium or sodium formate, ammonium sulfate, ammonium dihydrogen phosphate, calcium acetate, zinc acetate, tri-sodium citrate dihydrate, magnesium acetate, sodium acetate, magnesium chloride, cadmium chloride, ammonium acetate, sodium chloride and lithium sulfate. In one embodiment, the salt comprises a monovalent cation, e.g., sodium. In a preferred embodiment, the salt comprises a divalent cation. In an even more preferred embodiment, the salt comprises a calcium cation, a magnesium cation or a manganese cation. In a further preferred embodiment, the salt comprises a calcium divalent cation. In one embodiment, the salt is calcium chloride, calcium acetate, zinc acetate, sodium citrate, tri-sodium citrate dihydrate, magnesium chloride, lithium sulfate, sodium chloride, magnesium acetate, sodium acetate or a manganese salt, such as manganese acetate or manganese chloride. In a preferred embodiment, the salt is calcium acetate. Examples of other salts that comprise a divalent cation, such as a calcium cation, are known in the art, and include, inter alia, those listed in the 2000 Sigma catalog, herein incorporated by reference. Without wishing to be bound to any theory, it is thought that the salt cation may neutralize the negative charges on the lipopeptide, e.g., the four carboxylic acids of daptomycin. Organic precipitants include, inter alia, polyethylene glycols (PEGs) that can vary in average molecular weight from between 300 and 10,000, or polyethylene glycol monomethyl ether (PEG-MME). In a preferred embodiment, the organic precipitant is PEG 300, PEG 600, PEG 2000, PEG 4000, PEG 8000 or PEG 10,000.

The lipopeptide is precipitated or crystallized from a solution that is buffered to pH 5.0 to 9.5. In one embodiment, prior to being buffered, the solution has a pH of about 1.5, 2.0 or 3.0. In one embodiment, daptomycin or a daptomycin-related lipopeptide is precipitated or crystallized from a solution of approximately pH 5.5 to approximately pH 7.5. In another embodiment, the buffer has a pH of approximately 5.9 to approximately pH 6.3. In one embodiment, the buffered solution may be obtained by using a pH buffering agent. Examples of pH buffering agents include, without limitation, Tris, phosphate, citrate, HEPES, CHES, sodium acetate or 2-morpholinoethanesulfonic acid (MES), sodium borate, sodium cacodylate, imidazole and tri-sodium citrate dihydrate. In a preferred embodiment, the salt is sodium cacodylate, sodium acetate, tri-sodium citrate dihydrate, HEPES, MES, CHES, imidazole, calcium acetate and Tris-HCl. In a more preferred embodiment, the pH buffer is calcium acetate pH 6.1, sodium acetate pH 6.1, sodium cacodylate pH 6.5, tri-sodium citrate dihydrate pH 5.6, HEPES pH 7.5, imidazole pH 8, MES pH 6.0, calcium acetate pH 6 and Tris-HCl pH 8.5. In another embodiment, the solution may be buffered by using a salt that also has buffering capacity. In a preferred embodiment, the pH buffer is calcium acetate pH 6.1.

The lipopeptide is precipitated or crystallized using hanging drop vapor diffusion from a solution containing 2 to 40% low molecular weight or polyhydric alcohol, 0.001 to 0.5 M salt and 0.005 to 0.2 M pH buffering agent. In a preferred embodiment, the lipopeptide is precipitated or crystallized from a solution containing 3 to 30% low molecular weight or polyhydric alcohol, 0.01 to 0.3 M salt and 0.01 to 0.1 M pH buffering agent. In a more preferred embodiment, the lipopeptide is precipitated or crystallized from a solution containing 5 to 20% low molecular weight or polyhydric alcohol, 0.02 to 0.1 M salt and 0.02 to 0.07 M pH buffering agent. The solution provided may or may not include polyethylene glycol (PEG) or polyethylene glycol monomethyl ether (PEG-MME).

The lipopeptide is precipitated or crystallized using batch crystallization from a solution containing 65 to 95% low molecular weight or polyhydric alcohol, 0.001 to 0.5 M salt and 0.001 to 0.2 M pH buffering agent. In a preferred embodiment, the lipopeptide is precipitated or crystallized from a solution containing 70 to 90% low molecular weight or polyhydric alcohol, 0.005 to 0.04 M salt and 0.005 to 0.04 M pH buffering agent. In some embodiments, the lipopeptide is crystallized from a solution which also comprises 3-8% organic precipitant. In a more preferred embodiment, the lipopeptide is precipitated or crystallized from a solution containing 80 to 85% low molecular weight or polyhydric alcohol, 0.01 to 0.03 M salt and 0.01 to 0.03 M pH buffering agent. In some embodiments, the solution further comprises about 4 to 5% organic precipitant, e.g., PEG or PEG-MME. In other embodiment, the solution provided does not include polyethylene glycol (PEG) or polyethylene glycol monomethyl ether (PEG-MME).

The lipopeptide is precipitated or crystallized at a temperature from approximately 0° C. to approximately 30° C. to obtain precipitate or crystal formation, respectively. In a preferred embodiment, a lipopeptide is crystallized or precipitated at a temperature of approximately 20-30° C. In a more preferred embodiment, the mixture is crystallized or precipitated at approximately 23-28° C. In an even more preferred embodiment, the mixture is crystallized or precipitated at approximately 27° C. The mixture may be crystallized or precipitated for any time period that results in crystallization or precipitation, preferably approximately one hour to approximately two weeks. In a preferred embodiment, the mixture is stored for a period of approximately three hours to approximately 24 hours, more preferably approximately 8-18 hours.

Lipopeptide crystals or crystal-like particles may have a shape that is, without limitation, needle-like, rod-like, urchin-like, flake-like, plate-like or clusters thereof. In one embodiment, lipopeptide crystals or crystal-like particles are urchin-like, rod-like or needle-like. The shape of the crystal or crystal-like particle may be determined, inter alia, by optical or electron microscopy. In another embodiment, lipopeptide crystals or crystal-like particles may be any size that is at least approximately 0.5:m in diameter in any one dimension. In a more preferred embodiment, lipopeptide crystals or crystal-like particle are at least 5 µm, more preferably at least 10 µm. In an even more preferred embodiment, the lipopeptide crystals or crystal-like particles are at least 50 µm, more preferably at least 100 µm. The size of the crystal may be determined by any method known to one having ordinary skill in the art. See, e.g., United States Pharmacopeia (USP), pp. 1965-67.

The properties of a crystalline or crystal-like lipopeptide may be determined by any method known to one having ordinary skill in the art. The properties that can be determined include the crystalline or crystal-like lipopeptide's size, shape, birefringence properties, powder x-ray diffraction properties, solid state NMR properties, melting temperature and stability to heat, light, humidity, and degradation. In a preferred embodiment, one having ordinary skill in the art may determine whether a lipopeptide is crystalline by powder x-ray diffraction. Powder x-ray diffraction is highly useful for determining whether a preparation is crystalline when the sample is a randomly-oriented collection of small crystals. Diffraction by a mass of randomly-oriented microcrystals produces a series of lines or rings (dependent of the detector) characteristic of the molecule studied and its structure. In a preferred embodiment, powder diffraction is measured by an Automated Powder Diffraction instrument in order to determine whether a lipopeptide is crystalline. See, e.g., Atkins et al., *Physical Chemistry*, pp. 710-716 (1978), herein incorporated by reference for a discussion of the Debye-Scherrer method for powder diffraction. Any powder diffractometer instrument known in the art that is equipped with any detector for powder diffraction that known in the art could be used to measure the diffraction pattern.

In a preferred embodiment of the invention, a lipopeptide is crystallized or precipitated using a buffering agent between approximately pH 5.0 and 9.5, a salt and an alcohol at a temperature of approximately 24-28° C. for a period of approximately three to 24 hours. In a preferred embodiment, the salt is a buffering agent and comprises a divalent cation and the alcohol is a low molecular weight alcohol, and the pH is between approximately pH 5.5 and 7.5. In an even more preferred embodiment, the salt is a calcium salt, the alcohol is isopropanol and the pH is between approximately pH 5.9 and 6.3. In embodiments were the solution includes an organic precipitant, preferably the organic precipitant is PEG 4000 or PEG 8000. In another embodiment the lipopeptide is precipitated or crystallized from a solution containing 12 to 18% glycerol, 0.3 to 0.8 m salt, 0.03 to 0.08 m pH buffering agent, and 12-18% PEG 600. In a still further preferred embodiment, the lipopeptide is daptomycin or a daptomycin-related lipopeptide. Examples 2-3 provide methods for precipitating a highly pure crystal-like daptomycin. One having ordinary skill in the art, following the teachings of the instant specification, may modify the crystallization/precipitation conditions provided in the examples to crystallize or precipitate daptomycin, daptomycin-related lipopeptides, or other lipopeptides of interest. Further, although the teachings of the instant specification describe the use of a single crystallization or precipitation step in a process for purifying a lipopeptide, one having ordinary skill in the art following the teachings of the specification may use multiple crystallization or precipitation steps in a process for purifying a lipopeptide. It may be advantageous to employ multiple rounds of crystallization or precipitation as disclosed herein in order to further increase purity of the lipopeptide.

After crystallization or precipitation, one may collect the crystalline material or crystal-like precipitate by any method known in the art. In a preferred embodiment, the crystalline material or crystal-like precipitate is collected by centrifugation or filtration. In an even more preferred embodiment, the crystalline material or crystal-like precipitate is collected by filtration because filtration is easily incorporated into a large-scale process for producing a lipopeptide. After the crystalline material or crystal-like precipitate is collected, it may be washed to remove excess crystallizing or precipitating reagents. Any wash solvent known in the art may be chosen so long as it does not appreciably dissolve the crystalline material or crystal-like precipitate. An example of a wash solvent is provided in Example 12. After the crystalline material or crystal-like precipitate is washed, it may be dried by any method known in the art. Examples of drying methods include air-drying, lyophilization (freeze-drying) or desiccation. In a preferred method, the crystalline material or crystal-like precipitate is desiccated. See, e.g., Example 12. In another embodiment, the crystalline lipopeptide's stability may be determined by its residual antibiotic activity or its degradation. The antibiotic activity may be measured in a standard agar-diffusion assay against various bacterial strains. See, e.g., Example 32 of U.S. Pat. No. 4,537,717, specifically incorporated herein by reference. The amount of degradation can be measured by, inter alia, HPLC analysis, such as that described in International PCT Publication WO 01/53330, published Jul. 26, 2001. In a preferred embodiment, the stability of the crystalline lipopeptide is greater than that of the amorphous form of the lipopeptide. The stability of the crystalline lipopeptide may be determined by exposing the crystalline lipopeptide and an amorphous form thereof to heat, light, humidity, and measuring the degree of degradation of the crystalline form to that of the amorphous form.

Degradation of the lipopeptide may be measured by determining the biological activity of the lipopeptide or any applicable physical parameter. In one embodiment, degradation may be measured by determining a particular biological activity of a lipopeptide after it has been subjected to heat, light, humidity, changes in pH or extreme pH, and comparing it to the same biological activity of the lipopeptide prior to any tests of stability. The amount of degradation may be determined, for example, by determining the percentage of biological activity remaining after the test of stability. The percentage of remaining biological activity may be compared to that of an amorphous form of the lipopeptide that has been subjected to the same test. In one embodiment, if the lipopeptide is an antibiotic, the crystalline lipopeptide may be tested for its antibiotic activity both prior to and after a test of its stability and compared to an amorphous form that has been tested prior to and after a degradation test. In a preferred embodiment, the lipopeptide is daptomycin or a daptomycin-related lipopeptide, and the biological activity test determines the amount of antibiotic activity of the lipopeptides against gram-positive bacteria.

Degradation of a lipopeptide may also be measured by a physical assay. In one embodiment, degradation may be measured by determining the percentage of intact crystalline lipopeptide that remains after a test of its stability. The percentage of remaining intact lipopeptide may be compared to that of an amorphous form of the lipopeptide that has been subjected to the same test for stability. In a preferred embodiment, the degradation of the lipopeptide may be measured by HPLC, ultraviolet spectroscopy, infrared spectroscopy, NMR, or mass spectroscopy. In an even more preferred embodiment, HPLC is used to determine the percentage of intact lipopeptide that remains after a crystalline form of a lipopeptide has been subjected to a test of its stability.

Without wishing to be bound by any theory, applicants believe that daptomycin is crystallized by the methods described above. However, it is thought that washing and/or drying the daptomycin crystals causes the daptomycin crystalline material to revert to a non-crystalline but still crystal-like form. Nevertheless, even if the methods described above only precipitate rather than crystallize the daptomycin or other lipopeptide, the methods still are advantageous because the methods purify the lipopeptide.

The invention also provides a crystalline or crystal-like lipopeptide produced by the above-described methods. In one embodiment, the crystalline or crystal-like lipopeptide comprises a lower amount of one or more impurities compared to the lipopeptide before crystallization or precipitation. In one embodiment, crystalline or crystal-like lipopeptide is daptomycin that comprises a lower level of anhydro-daptomycin and/or the β-isomer of daptomycin compared to daptomycin before crystallization or precipitation. In another embodiment, crystalline or crystal-like daptomycin comprises a lower level of all impurities compared to amorphous daptomycin. Similarly, in another embodiment, the crystalline or crystal-like lipopeptide is a daptomycin-related lipopeptide, as described above, which comprises a lower level of one or more impurities compared to an amorphous form of the daptomycin-related lipopeptide. In yet another embodiment, the crystalline or crystal-like daptomycin-related lipopeptide comprises a lower level of all impurities compared to an amorphous form of the daptomycin-related lipopeptide.

The crystalline or crystal-like lipopeptide produced by the method described above likely comprises monovalent or divalent cations and water. In a preferred embodiment, the crystalline or crystal-like lipopeptide is daptomycin or daptomycin-related lipopeptide that comprises a divalent cation. In a more preferred embodiment, the divalent cation is a calcium cation. In an even more preferred embodiment, the crystalline or crystal-like daptomycin or daptomycin-related lipopeptide comprises approximately 1-10% by weight of a divalent calcium cation and approximately 0-15% by weight of water as determined by atomic absorption or thermal gravity analysis. In a further preferred embodiment, the crystalline or crystal-like lipopeptide is daptomycin that comprises approximately 5% by weight of a divalent calcium cation and approximately 10% by weight of water; by HPLC analysis, the purity of the crystalline or crystal-like daptomycin is at least 95%, 96%, 97% or 98% or is any purity between 95-98%, relative to related substances and organic contaminants. Alternatively, the crystalline or crystal-like daptomycin or daptomycin-related lipopeptide comprises a monovalent cation such as sodium. Without wishing to be bound by any theory, it is thought that daptomycin or a daptomycin-related lipopeptide may form a salt with the monovalent or divalent cation when it crystallizes or precipitates.

The crystalline form of the lipopeptide may exhibit an increased solubility in a solution or an increased rate of reconstitution in a solution than an amorphous form of the lipopeptide. One may measure whether the crystalline lipopeptide exhibits an increased solubility or increased reconstitution rate by any method known in the art. For instance, one may dissolve a defined amount of a crystalline lipopeptide in an aqueous solution and measure the concentration of the dissolved lipopeptide and compare it to the concentration of dissolved lipopeptide that has been prepared by dissolving the same amount of amorphous lipopeptide in an aqueous solution. Similarly, one may measure the reconstitution rate of a crystalline lipopeptide by adding the crystalline lipopeptide to an aqueous solution and then measuring the concentration of dissolved lipopeptide over time and comparing it to the reconstitution rate of an amorphous lipopeptide that has been measured in the same way. The concentration of lipopeptide is measured by HPLC.

The methods described above provide for the production of crystalline or crystal-like lipopeptides that are more pure than the amorphous lipopeptide from which they are crystallized or precipitated. In one embodiment, the lipopeptide is daptomycin or a daptomycin-related lipopeptide. In another embodiment, daptomycin or a daptomycin-related lipopeptide has a purity of no more than 92% before crystallization and has a purity of at least approximately 95%, 96%, 97% or 98% purity, or any purity between 95-98%, after crystallization or precipitation as a crystal-like lipopeptide. In a still further preferred embodiment, daptomycin or a daptomycin-related lipopeptide has a purity of no more than 90% before crystallization and has a purity of approximately at least 97% or 98% after crystallization.

In another embodiment, the daptomycin has a purity of no more than 80%, preferably no more than 70% and more preferably no more than 60% purity before crystallization or precipitation, and has at least approximately 95%, 96%, 97% or 98% purity, or any purity between 95-98%, after purification. In another embodiment, the daptomycin has a purity of no more than 50%, preferably no more than 40%, more preferably no more than 30% purity before crystallization and has at least approximately 95%, 96%, 97% or 98% purity, or any purity between 95-98%, after purification by crystallization or precipitation. Further preferred is an embodiment in which daptomycin has a purity of no more than 20%, more preferably no more than 15%, even more preferably no more than 10% purity before crystallization and has at least approximately 95%, 96%, 97% or 98% purity, or any purity between 95-98%, after purification.

In a more preferred embodiment, the lipopeptide is daptomycin. A daptomycin preparation may be obtained by any method disclosed, e.g., in any one U.S. Pat. Nos. RE32,333, RE32,455, 4,800,157, RE32,310, RE32,311, 4,537,717, 4,482,487, 4,524,135, 4,874,843, 4,885,243 or 5,912,226, which are herein incorporated specifically by reference. A daptomycin preparation may also be obtained by one of the methods described in International PCT Publication WO 01/53330, published Jul. 26, 2001. After the lipopeptide preparation is prepared, the lipopeptide preparation is crystallized or precipitated following the teachings of the specification described herein to produce a crystalline or crystal-like lipopeptide that is more pure or that contains lower levels of specific impurities, e.g., anhydro-daptomycin, than the lipopeptide preparation from which it is prepared.

Processes for Producing Purified Lipopeptides from Fermentation Cultures

Another embodiment of the present invention is drawn to a process combining process chromatography steps and crystallization or precipitation to produce a purified lipopeptide. In a preferred embodiment, the method comprises the steps of producing a lipopeptide by any method known in the art, such as fermentation of a naturally-occurring or recombinant organism, and then subjecting the lipopeptide preparation to any one or more purification methods such as microfiltration, anion exchange chromatography, hydrophobic interaction chromatography, and/or size exclusion chromatography (either via traditional size exclusion chromatographic media or via ultrafiltration) to produce a lipopeptide preparation that has been partially purified, and then crystallizing or precipitating the lipopeptide preparation to obtain a purified crystalline or crystal-like lipopeptide. In a preferred embodiment, the lipopeptide is daptomycin or a daptomycin-related lipopeptide. The steps regarding fermentation, microfiltration, anion exchange chromatography, hydrophobic interaction chromatography and ultrafiltration are disclosed in the art, e.g., in any one U.S. Pat. Nos. RE32,333, RE32,455, 4,800,157, RE32,310, RE32,311, 4,537,717, 4,482,487, 4,524,135, 4,874,843, 4,885,243 or 5,912,226, in International Publication WO 01/53330, published Jul. 26, 2001.

The method optionally comprises the step of collecting and/or washing the crystalline or crystal-like material after the crystallization or precipitation step. In a preferred embodiment, the crystalline lipopeptide preparation may be collected by filtration. In another embodiment, the crystalline or crystal-like material is dried.

In one embodiment, the purification method comprises fermenting *Streptomyces roseosporus* to obtain a fermentation culture containing daptomycin. In one embodiment, the *S. roseosporus* may be fermented as described in U.S. Pat. No. 4,885,243. In another embodiment, the fermentation conditions in which the A-21978$C_0$-containing crude product is produced by *Streptomyces roseosporus* is altered in order to increase daptomycin production and decrease impurities and related contaminants produced by the *S. roseosporus* fermentation culture as described in International PCT Publication WO 01/53330, published Jul. 26, 2001. The WO 01/53330 publication describes fermenting *S. roseosporus* as described in the '243 patent with the modification that the decanoic acid feed is kept at the lowest levels possible without diminishing the overall yield of the fermentation.

Alternatively, daptomycin may be obtained by fermenting a bacterial strain or other producing organism that recombinantly produces daptomycin. In one embodiment, the recombinant bacterial strain or other recombinant organism comprises the daptomycin biosynthetic gene cluster. In another embodiment, the daptomycin biosynthetic gene cluster or a portion thereof is introduced into the organism or bacterial strain via a bacterial artificial chromosome (BAC). In another embodiment, the recombinant bacterial strain used is *S. roseosporus* or *S. lividans* comprising a BAC containing the daptomycin biosynthetic gene cluster. U.S. Provisional Application 60/272,207, filed Feb. 28, 2001 describes the daptomycin biosynthetic gene cluster from *S. roseosporus* and uses thereof, and is hereby incorporated by reference in its entirety.

Figure 11:
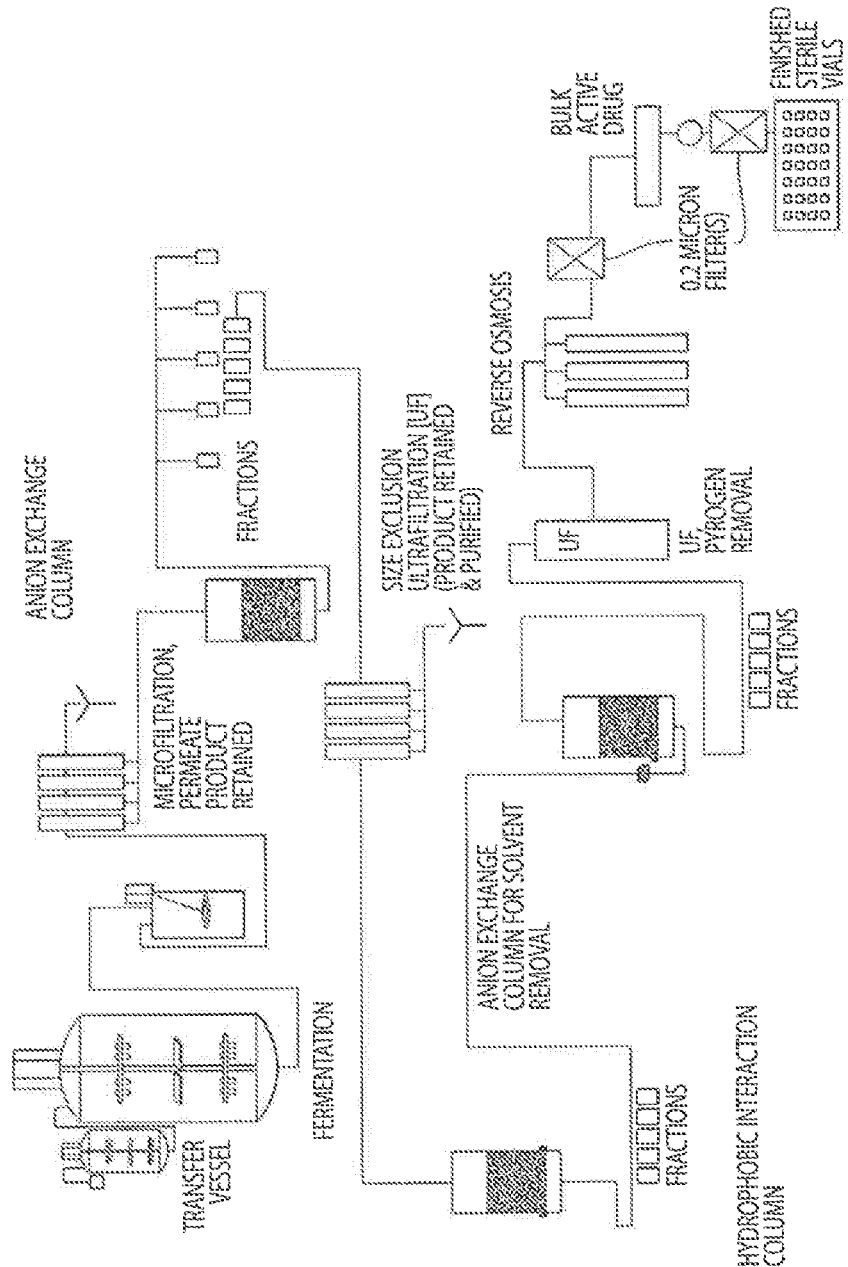
FIG. 11 shows a flow chart of an exemplary manufacturing method that does not use crystallization or precipitation. The manufacturing method uses bacterial fermentation to produce a fermentation culture containing daptomycin, and then purification of daptomycin using microfiltration, size exclusion ultrafiltration, hydrophobic interaction chromatography, anion exchange chromatography for solvent removal, ultrafiltration for pyrogen removal, reverse osmosis and filling vials with daptomycin. See, e.g., International PCT Publication WO 01/44274, published Jun. 21, 2001, herein incorporated by reference for a detailed description of this type of method.
Figure 12:
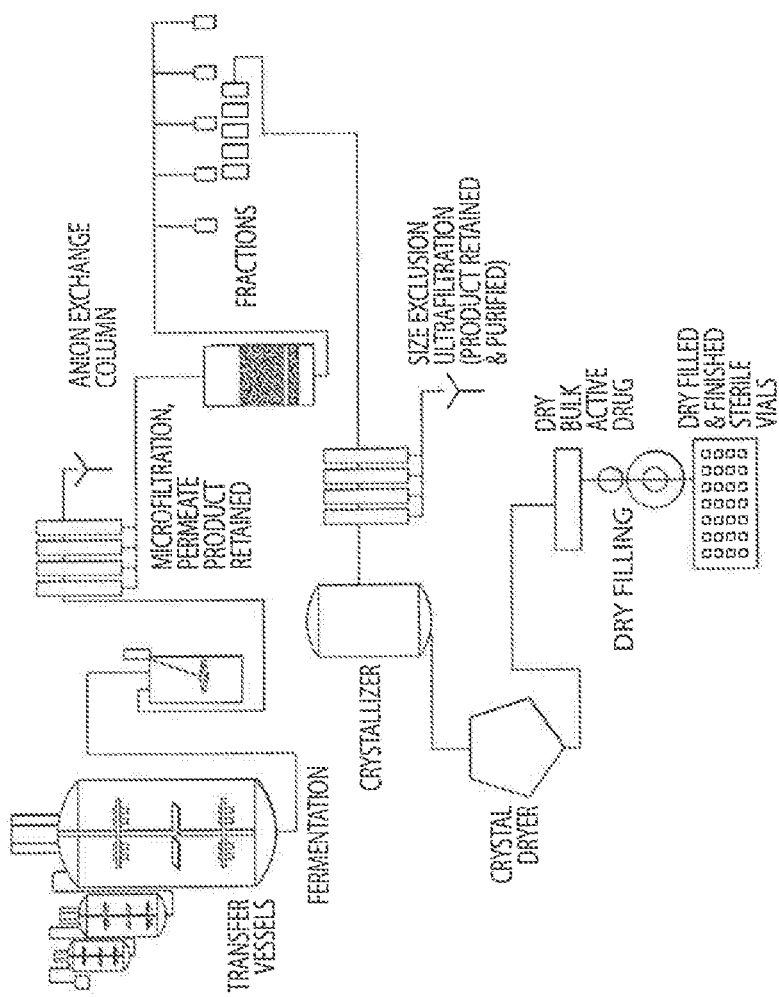
FIG. 12 shows a flow chart of an exemplary manufacturing method of a lipopeptide compound comprising the steps of fermentation, microfiltration, anion exchange chromatography, size exclusion ultrafiltration, crystallization or precipitation, crystal or precipitate drying, and dry filling of vials with the compound. See, e.g., Example 13.
Figure 13:
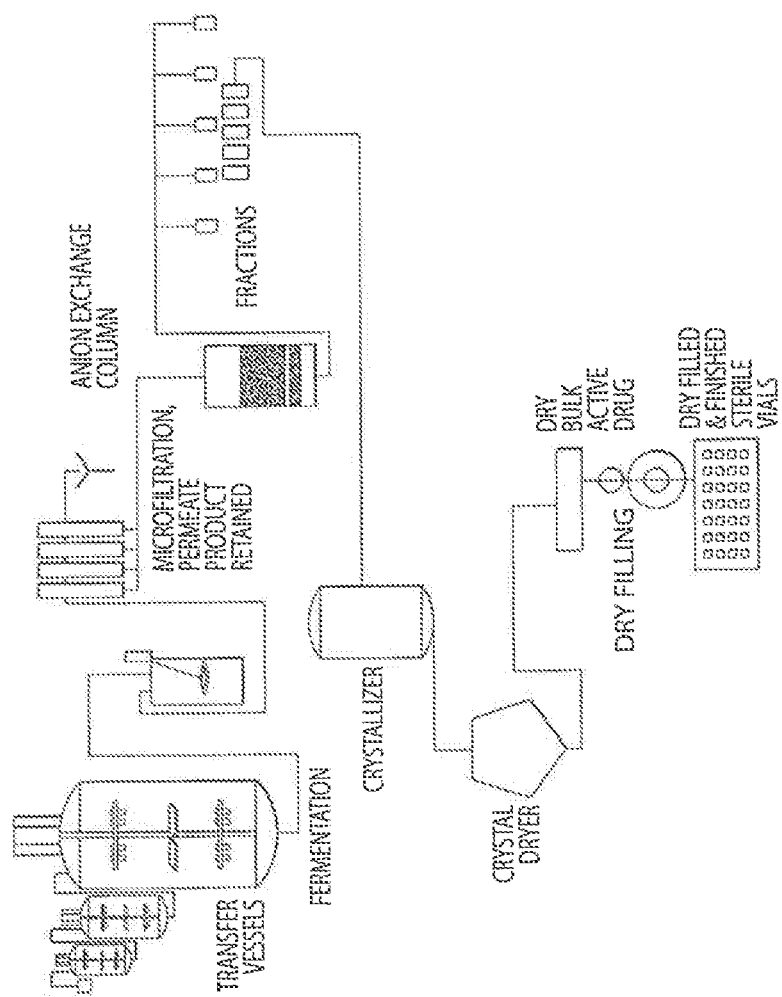
FIG. 13 shows a flow chart of an exemplary manufacturing method of a lipopeptide compound comprising the steps of fermentation, microfiltration, anion exchange chromatography, crystallization or precipitation, crystal or precipitate drying, and dry filling of vials with the compound. See, e.g., Example 14.
Figure 14:
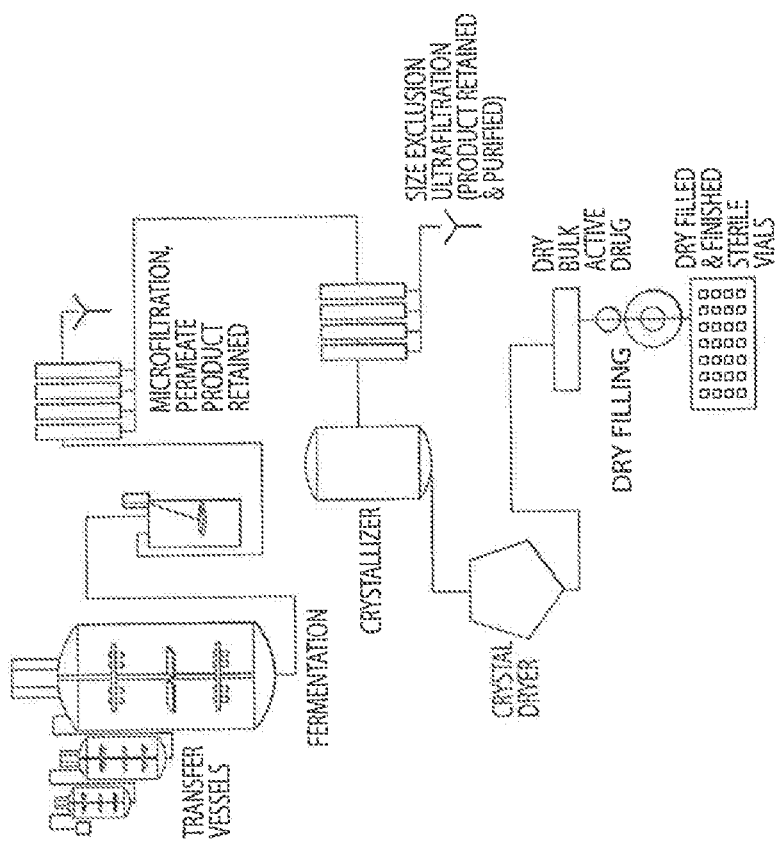
FIG. 14 shows a flow chart of an exemplary manufacturing method of a lipopeptide compound comprising the steps of fermentation, microfiltration, size exclusion ultrafiltration, crystallization or precipitation, crystal or precipitate drying, and dry filling of vials with the compound. See, e.g., Example 15.
Figure 15:
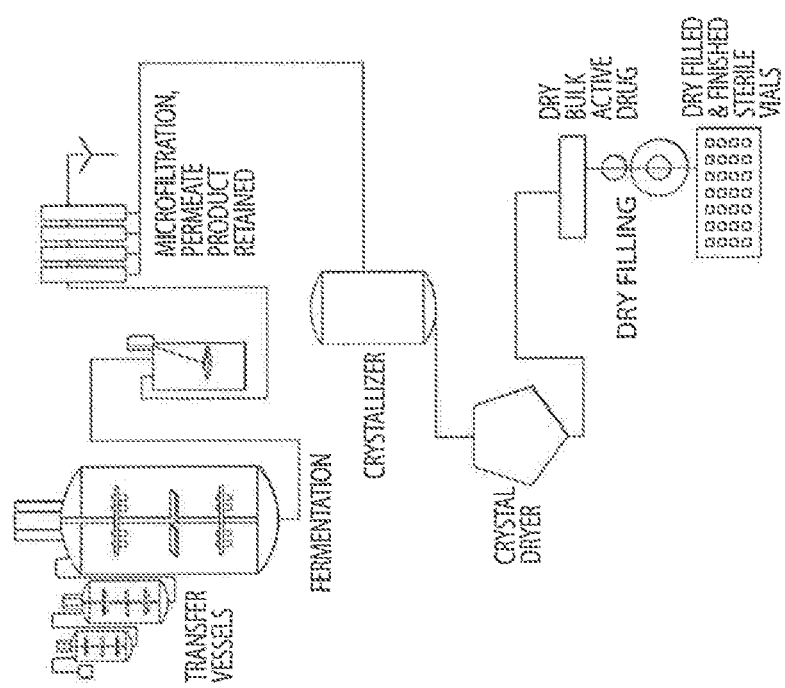
FIG. 15 shows a flow chart of an exemplary manufacturing method of a lipopeptide compound comprising the steps of fermentation, microfiltration, crystallization or precipitation, crystal or precipitate drying, and dry filling of vials with the compound. See, e.g., Example 16.
Figure 16:
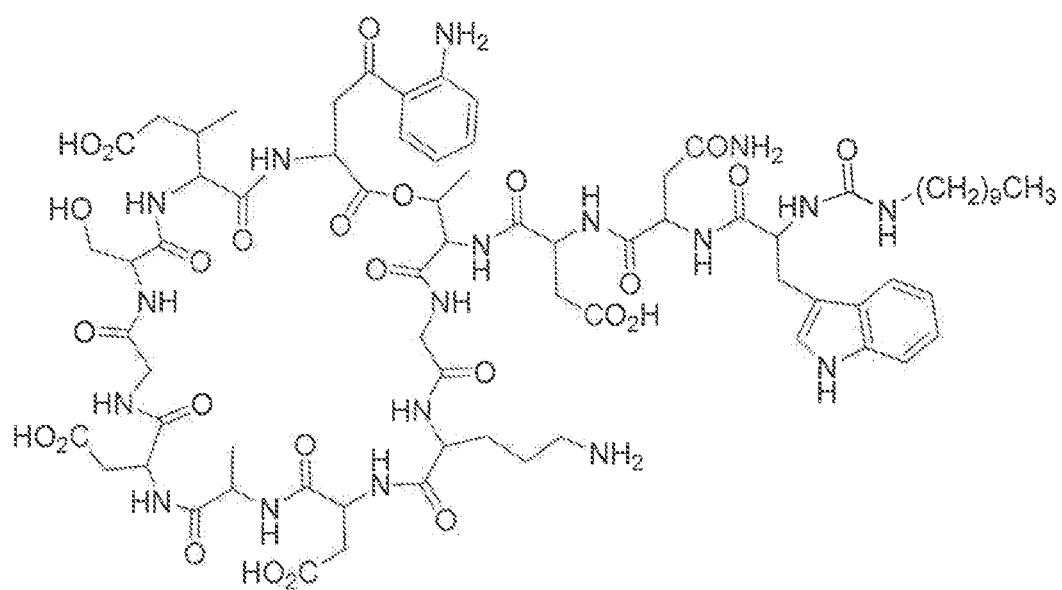
FIG. 16 depicts the structure of CB-131547, a cyclic lipopeptide analog of daptomycin

After fermentation, the fermentation broth is clarified by centrifugation, microfiltration or extraction, as is known in the art or as described in the WO 01/53330 publication. In a preferred embodiment, the clarification is performed by microfiltration. See, e.g., Examples 13-16 and FIGS. 11-15. FIG. 11 shows an exemplary manufacturing process that does not use crystallization or precipitation.

After the fermentation broth is clarified, the concentration of daptomycin in the broth is approximately 5-10%. In one embodiment of the invention, the daptomycin preparation is subjected to a crystallization/precipitation method described above directly subsequent to microfiltration. In one embodiment, crystallization or precipitation is performed under sterile conditions. After crystallization or precipitation is complete, the crystalline or crystal-like daptomycin is optionally collected, washed and dried, as described in further detail below. The dry bulk active drug may then be used to dry fill sterile vials. See, e.g., Example 16 and FIG. 12.

After clarification of the fermentation broth, the lipopeptide may be enriched in the preparation by anion exchange chromatography, as is known in the art or as described in the WO 01/53330 publication or herein. See, e.g., Examples 13-14 and FIGS. 12-13. After anion exchange chromatography, the purity of daptomycin in the broth is approximately 35-40%. In one embodiment of the invention, the daptomycin preparation is then subjected to a crystallization or precipitation method described above directly subsequent to anion exchange chromatography. In one embodiment, crystallization or precipitation is performed under sterile conditions. After crystallization or precipitation is complete, the crystalline or crystal-like daptomycin is optionally collected, washed and dried as described below. The dry bulk active drug may then be used to dry fill sterile vials. See, e.g., Example 14 and FIG. 13.

In another embodiment of the invention, the daptomycin preparation is subjected to size exclusion ultrafiltration after anion exchange chromatography. Size exclusion ultrafiltration is described in the WO 01/53330 publication. The application published Jul. 26, 2001 describes a method of depyrogenating, filtering and concentrating the daptomycin using an ultrafiltration membrane of 10,000 to 30,000 nominal molecular weight (NMW). The application discloses a method in which the lipopeptide passes through the ultrafiltration membrane while large molecular weight impurities, such as endotoxins, are retained by the filter. After the lipopeptide has passed through the membrane, the pH, temperature and/or salt concentration of the lipopeptide solution are altered such that the lipopeptides form micelles. The lipopeptide solution is then filtered on the ultrafiltration membrane under conditions in which the lipopeptide micelles are retained on the membrane while smaller impurities pass through the filter. In this manner, the lipopeptide is further purified. The application discloses the conditions under which lipopeptide micelles may be formed and disassociated as well as methods for filtering the lipopeptide solution to obtain a more purified lipopeptide application. In an even more preferred embodiment, the lipopeptide is daptomycin or a daptomycin-related lipopeptide. The lipopeptide may then be crystallized, as described herein. After both anion exchange chromatography and size exclusion ultrafiltration, daptomycin purity is approximately 80-90%. As discussed above, the daptomycin preparation is then subjected to a crystallization/precipitation method described above, preferably under sterile conditions. The crystalline or crystal-like daptomycin may be optionally collected, washed, dried and used to dry fill vials as described below. See, e.g., Example 13 and FIG. 12.

In another embodiment of the invention, the crude daptomycin preparation is subjected to size exclusion ultrafiltration without anion exchange chromatography. After size exclusion ultrafiltration, daptomycin purity is approximately 35-40%. The lipopeptide may then be crystallized or precipitated as described herein, preferably by sterile methods. As discussed above, the crystalline or crystal-like daptomycin may be collected, washed, dried and used to dry fill sterile vials. See, e.g., Example 15 and FIG. 14.

In an alternative embodiment, the lipopeptide preparation is subjected to hydrophobic interaction chromatography (HIC), such as is described in the WO 01/53330 publication, after either the anion exchange chromatography or the size exclusion filtration. The lipopeptide may then be crystallized or precipitated as described herein.

After crystallization or precipitation, the crystalline or crystal-like lipopeptide may be collected by a method described herein, e.g., by filtration or centrifugation. The crystalline or crystal-like lipopeptide is optionally washed to remove residual crystallization or precipitation solvent. A method of washing crystals or crystal-like material are described below. See, e.g., Example 3. The washed or unwashed crystal or crystal-like material may be dried. The drying may be performed by any method known in the art, including, without limitation, vacuum drying, spray drying, tray drying or lyophilization. In one embodiment, the drying is performed under sterile conditions. In another embodiment, the drying is performed by vacuum drying. In a more preferred embodiment, the drying is performed using a 0.65 m$^3$ Klein Hastelloy-B double cone vacuum dryer or an equivalent apparatus. The dried crystalline or crystal-like lipopeptide is stable and is easily stored.

In one embodiment, vials are filled with any convenient amount of the dried crystalline or crystal-like lipopeptide. In one embodiment, the vials are filled under sterile conditions and then stoppered. In another embodiment, the vials are filled with 50 to 5000 mg each of the dried crystalline or crystal-like lipopeptide. In another embodiment, the vials are filled with 100 to 1000 mg each. In another embodiment, the vials are filled with 200 to 500 mg each. In another embodiment, the dried crystalline or crystal-like lipopeptide is used for bulk packaging of the lipopeptide. The bulk packaging is usually greater than 5000 mg each of the dried crystalline or crystal-like lipopeptide. In one embodiment, the bulk packaging is performed under sterile conditions.

In one embodiment, the crystallization or precipitation step is performed under sterile conditions. In this embodiment, sterile crystallization or precipitation reagents and a sterile, controlled working environment are used. In one embodiment, the lipopeptide is filtered on a ultrafiltration membrane, as disclosed above, before being mixed with the sterile crystallization/precipitation reagents. After crystallization or precipitation, the crystalline or crystal-like lipopeptide preparation is collected by centrifugation or filtration under sterile conditions. In one embodiment, the lipopeptide preparation is collected by sterile filtration. In another embodiment, the crystalline or crystal-like lipopeptide is sterilized after it has been collected. Methods of sterile crystallization, precipitation and filtration as well as methods of sterilizing a final pharmaceutical product are known in the art. See, e.g., *Remington: The Science and Practice of Pharmacy*, Easton, Pa.: Mack Publishing Company (1995), pp. 1474-1487, herein incorporated by reference.

In another embodiment, the crystalline or crystal-like lipopeptide is not dried. In this embodiment, the crystalline or crystal-like lipopeptide is preferably stored in a solution that preserves the crystalline or crystal-like nature of the lipopeptide. Vials may be filled with the lipopeptide and solution under sterile or nonsterile conditions. In one embodiment, the conditions are sterile. Alternatively, the crystalline or crystal-like lipopeptide and solution may be used to fill bulk packaging.

Figure 10:
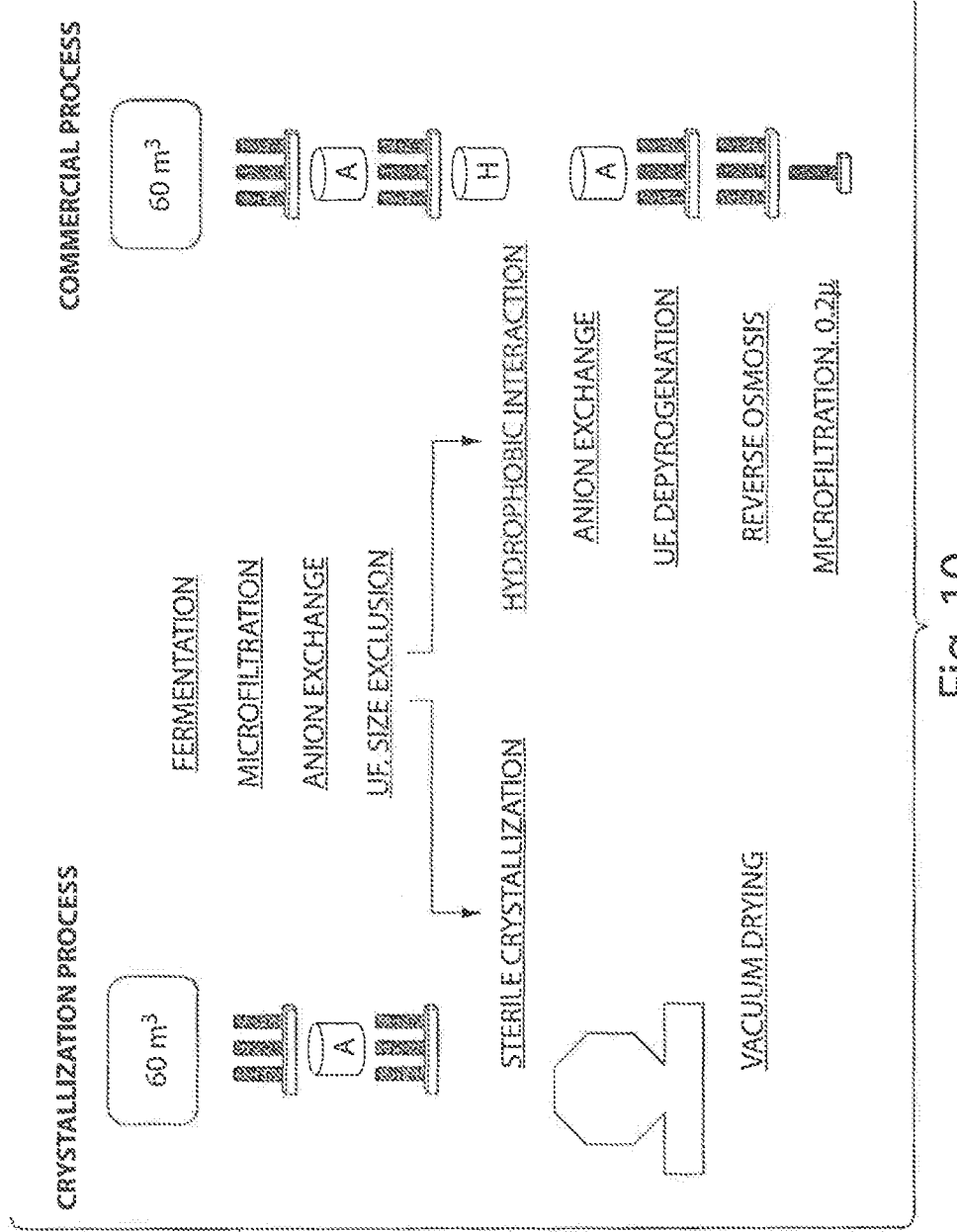
FIG. 10 shows a flow chart of an exemplary method for crystallization.

FIGS. 10 and 11 provide flowcharts describing an exemplary daptomycin manufacturing protocol using crystallization. The incorporation of sterile crystallization into the manufacturing protocol shortens the protocol considerably and eliminates 3 to 4 steps in the process.

Crystalline or Crystal-Like Lipopeptides, Pharmaceutical Compositions and Methods of Use Thereof Another object of the instant invention is to provide crystalline or crystal-like lipopeptides or salts thereof, as well as pharmaceutical formulations comprising a crystalline or crystal-like lipopeptide or its salts. In one embodiment, the crystalline or crystal-like lipopeptide is daptomycin. However, all reference herein to crystalline or crystal-like lipopeptides specifically contemplates daptomycin, a daptomycin-related molecule, including, inter alia, daptomycin, A54145 and a daptomycin-related lipopeptide, as disclosed above.

Daptomycin crystals or crystal-like particles, as well as other lipopeptide crystals or crystal-like particles may have a shape such as, inter alia, a needle-like shape, a plate-like shape, a lath-like shape, an equant-like shape, an urchin-like shape or a rod-like shape. In one embodiment, daptomycin crystals or crystal-like particles have an urchin-like, needle-like or rod-like shape. The size of the crystals or crystal-like particles may range from approximately 0.5 μm to greater than 100 μm. In one embodiment, the particle size is at least 5 μm or greater. In a more preferred embodiment, the particle size is at least 10 μm or greater, more preferably at least 50 μm. In an even more preferred embodiment, the particle size is at least 100 μm.

Figure 6:
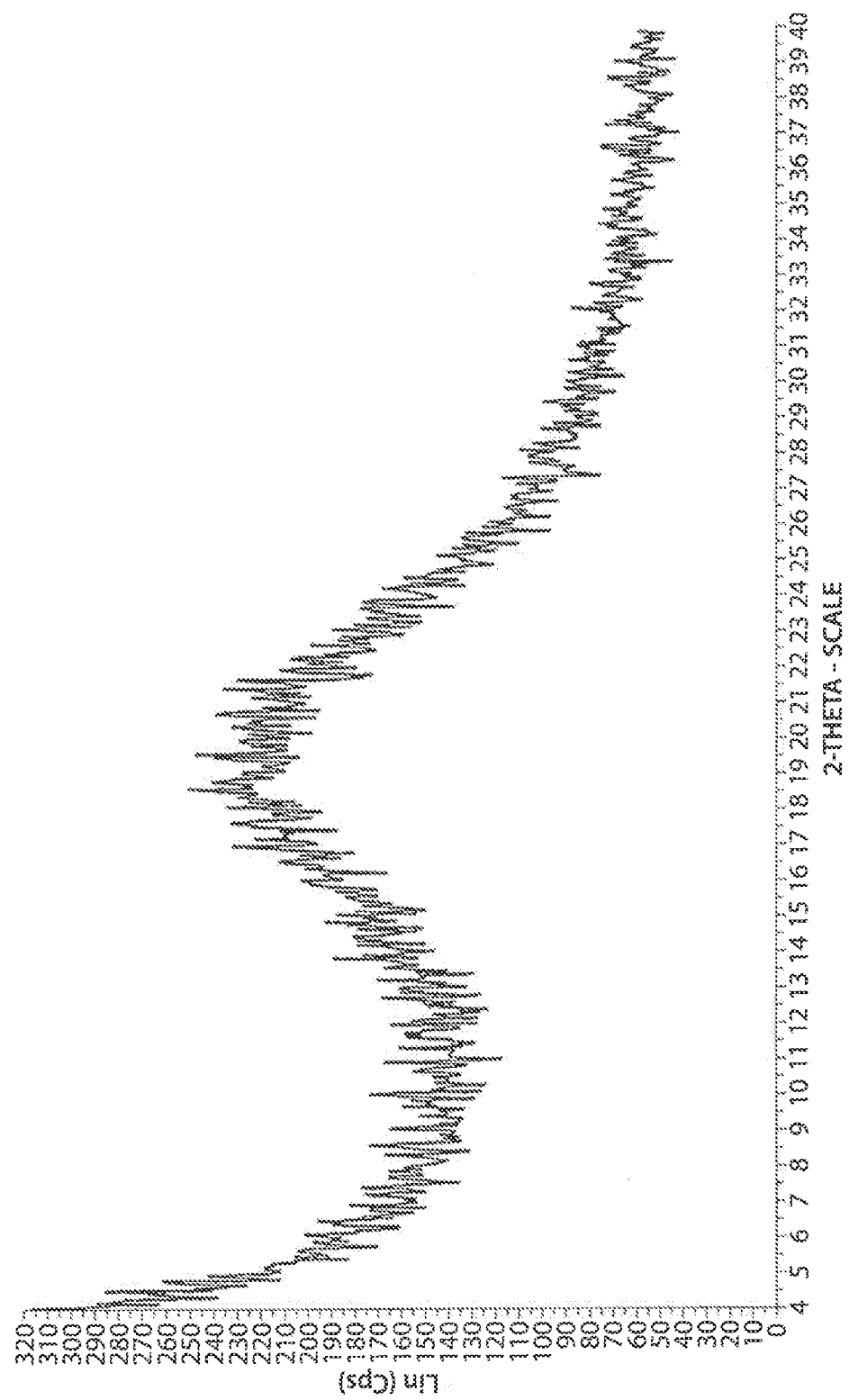
FIG. 6 shows an x-ray powder diffraction pattern for amorphous daptomycin.
Figure 7:
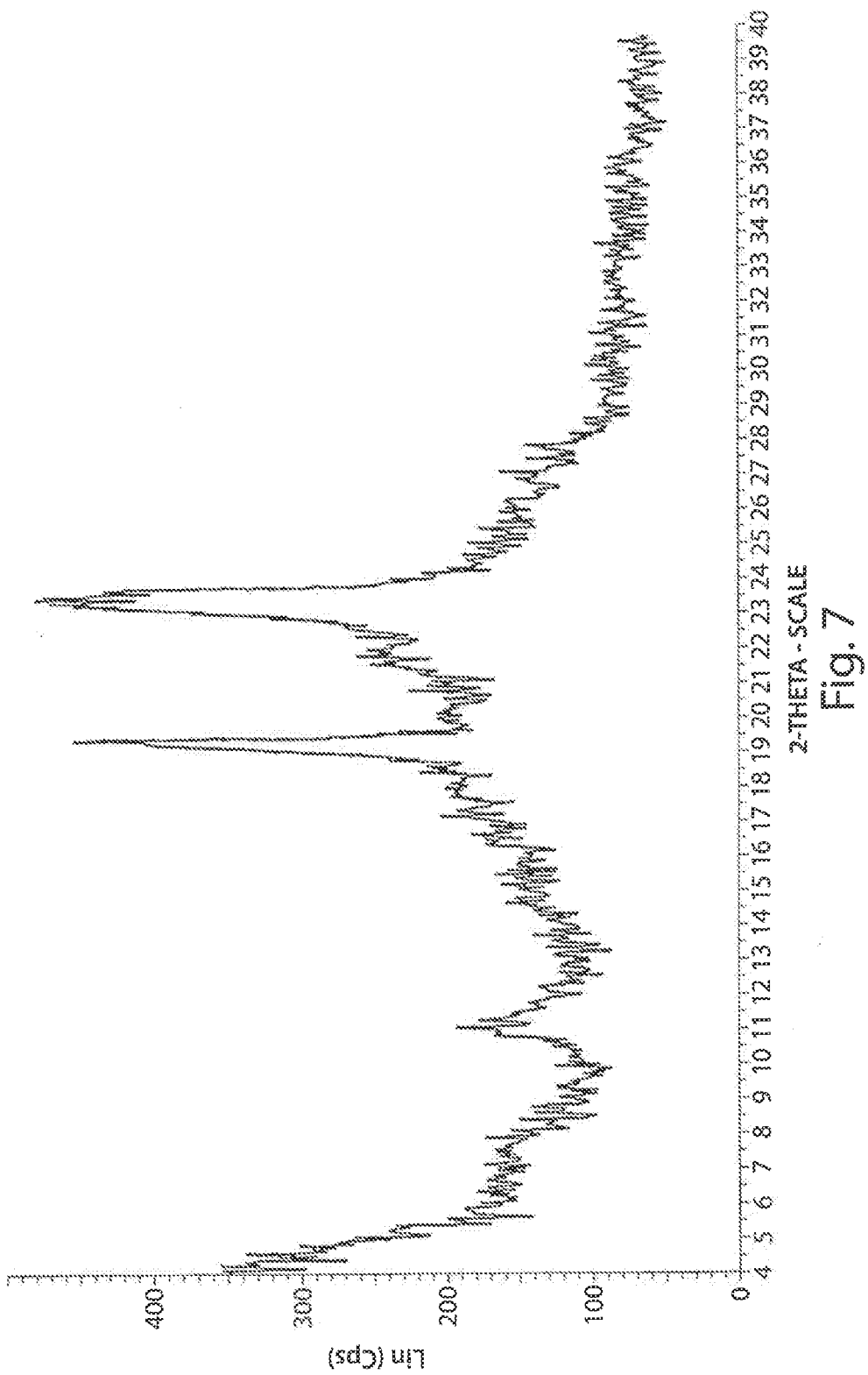
FIG. 7 shows an x-ray powder diffraction pattern for a daptomycin crystal produced by the protocol described in Example 7.
Figure 8:
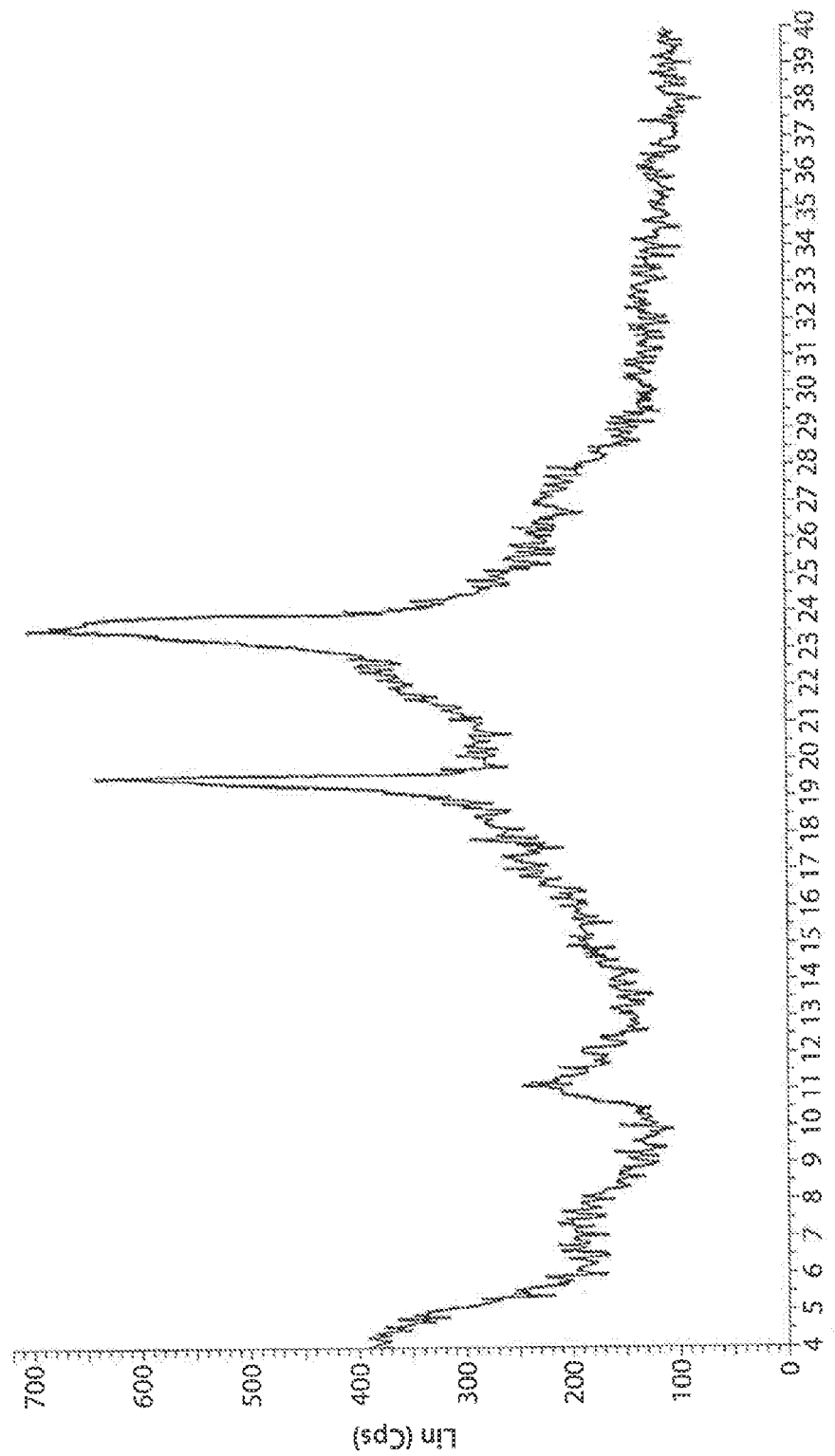
FIG. 8 shows an x-ray powder diffraction pattern for a second sample of a daptomycin crystal produced by the protocol described in Example 7.

Further, in one embodiment, daptomycin crystals have an x-ray diffraction pattern as shown in FIGS. 6, 7 and 8. In another embodiment, the lipopeptide crystal exhibits a different melting point than the amorphous form of the lipopeptide.

In one embodiment of the invention, a crystalline form of a lipopeptide exhibits a stability that is equal to or greater than the amorphous form of the lipopeptide. In a preferred embodiment, the crystalline form is daptomycin or a daptomycin-related lipopeptide. In another preferred embodiment, the crystalline lipopeptide is sterile. In another preferred embodiment, the stability of the crystalline lipopeptide is greater than the amorphous form of the lipopeptide. The crystalline lipopeptide may exhibit higher stability to heat, light, degradation or humidity than the amorphous form. The stability of the lipopeptide may be measured by any means including, e.g., antibiotic activity, degradation of the lipopeptide or conversion of daptomycin to anhydro-daptomycin or the β-isomer of daptomycin. In another embodiment of the invention, the crystalline form of the lipopeptide may be more quickly reconstituted in aqueous solution than the amorphous form of the lipopeptide.

Crystalline or crystal-like lipopeptides, such as daptomycin or a daptomycin-related lipopeptide, pharmaceutically-acceptable salts, esters, amides, ethers and protected forms thereof, can be formulated for oral, intravenous, intramuscular, subcutaneous, aerosol, topical or parenteral administration for the therapeutic, empirical or prophylactic treatment of diseases, particularly bacterial infections. Reference herein to "crystalline or crystal-like lipopeptides" or "crystalline or crystal-like daptomycin" includes pharmaceutically acceptable salts thereof. Crystalline or crystal-like lipopeptides, such as daptomycin, may be particularly advantageous for pharmaceutical compositions because they can be easily formulated as micronized particles of microspheres, which permits the facile preparation of enterically coated lipopeptides for oral delivery, pharmaceutical compositions for aerosol delivery to, e.g., the lung, and the preparation of lipopeptides formulations for sustained release. Crystalline or crystal-like lipopeptides and crystalline or crystal-like daptomycin may also be more readily dissolved in aqueous solution.

Crystalline or crystal-like lipopeptides, including daptomycin or daptomycin-related lipopeptides can be formulated using any pharmaceutically acceptable carrier or excipient that is compatible with daptomycin or with the lipopeptide of interest. See, e.g., Handbook of Pharmaceutical Additives: An International Guide to More than 6000 Products by Trade Name, Chemical, Function, and Manufacturer, Ashgate Publishing Co., eds., M. Ash and I. Ash, 1996; The Merck Index: An Encyclopedia of Chemicals, Drugs and Biologicals, ed. S. Budavari, annual; Remington's Pharmaceutical Sciences, Mack Publishing Company, Easton, Pa.; Martindale: The Complete Drug Reference, ed. K. Parfitt, 1999; and Goodman & Gilman's The Pharmaceutical Basis of Therapeutics, Pergamon Press, New York, N.Y., ed. L. S. Goodman et al.; the contents of which are incorporated herein by reference, for a general description of the methods for administering various antimicrobial agents for human therapy. Compounds of this invention can be mixed with conventional pharmaceutical carriers and excipients and used in the form of tablets, capsules, elixirs, suspensions, syrups, wafers, creams and the like. Compounds of this invention may also be mixed with other therapeutic agents and antibiotics, such as discussed herein. The compositions comprising a compound of this invention will contain from about 0.1 to about 90% by weight of the active compound, and more generally from about 10 to about 30%.

The compositions of the invention can be delivered using controlled (e.g., capsules) or sustained release delivery systems (e.g., bioerodable matrices). Exemplary delayed release delivery systems for drug delivery that are suitable for administration of the compositions of the invention are described in U.S. Pat. No. 4,452,775 (issued to Kent), U.S. Pat. No. 5,239,660 (issued to Leonard), U.S. Pat. No. 3,854,480 (issued to Zaffaroni).

The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral use, solid formulations such as tablets and capsules are particularly useful. Sustained release or enterically coated preparations may also be devised. In another embodiment, crystalline or crystal-like lipopeptides may be supplied in combination with a carrier composition that enhances the oral availability of the lipopeptide. In a preferred embodiment, the crystalline or crystal-like lipopeptide is daptomycin. For pediatric and geriatric applications, suspensions, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Oral liquid preparations may comprise lipopeptide micelles or monomeric forms of the lipopeptide. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, a water soluble form of a compound of this invention can be dissolved in any of the commonly used intravenous fluids and administered by infusion. Intravenous formulations may include carriers, excipients or stabilizers including, without limitation, calcium, human serum albumin, citrate, acetate, calcium chloride, carbonate, and other salts. Intravenous fluids include, without limitation, physiological saline or Ringer's solution. Daptomycin or other lipopeptides also may be placed in injectors, cannulae, catheters and lines.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The crystalline or crystal-like lipopeptides can be dissolved in polyethylene glycol, propylene glycol, ethanol, corn oil, benzyl alcohol, sodium chloride, and/or various buffers. For intramuscular, parenteral or intravenous preparations, a sterile formulation of a crystalline or crystal-like lipopeptide compound or a suitable soluble salt form of the compound, for example the hydrochloride salt, can be dissolved and administered in a pharmaceutical diluent such as Water-for-Injection (WFI), physiological saline or 5% glucose. A suitable insoluble form of the crystalline or crystal-like lipopeptide also may be prepared and administered as a suspension in an aqueous base or a pharmaceutically acceptable oil base, e.g., an ester of a long chain fatty acid such as ethyl oleate.

Injectable depot forms may be made by forming microencapsulated matrices of the crystalline or crystal-like lipopeptide in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in microemulsions that are compatible with body tissues.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient. For topical preparations, a sterile formulation comprising a crystalline or crystal-like lipopeptide, such as crystalline or crystal-like daptomycin, a suitable salt form thereof, may be administered in a cream, ointment, spray or other topical dressing. Topical preparations may also be in the form of bandages that have been impregnated with a lipopeptide composition.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

For aerosol preparations, a sterile formulation of a crystalline or crystal-like lipopeptide or a salt form of the compound may be used in inhalers, such as metered dose inhalers, and nebulizers. Aerosolized forms may be especially useful for treating respiratory infections, such as pneumonia and sinus-based infections.

Alternatively, the compounds of the present invention can be in powder crystalline or crystal-like form for reconstitution in the appropriate pharmaceutically acceptable carrier at the time of delivery. In another embodiment, the unit dosage form of the compound can be a solution of the compound or a salt thereof in a suitable diluent in sterile, hermetically sealed ampules. The concentration of the compound in the unit dosage may vary, e.g. from about 1 percent to about 50 percent, depending on the compound used and its solubility and the dose desired by the physician. If the compositions contain dosage units, each dosage unit preferably contains approximately from 10-5000 mg of the active material, more preferably 50 to 1000 mg, and even more preferably 100 to 500 mg. For adult human treatment, the dosage employed preferably ranges from 100 mg to 3 g, per day, depending on the route and frequency of administration.

In a further aspect, this invention provides a method for treating an infection caused by a gram-positive bacteria in a subject. In a preferred embodiment, the method may be used to treat an infection caused by a gram-positive bacteria. The term "treating" is defined as administering, to a subject, a therapeutically-effective amount of a compound of the invention, both to prevent the occurrence of an infection and to control or eliminate an infection, e.g., an established infection. The term "subject", as described herein, is defined as a mammal, a plant or a cell culture. As used herein, the phrase "therapeutically-effective amount" means an amount of daptomycin, daptomycin-related lipopeptide or other antibacterial lipopeptide according to the present invention that prevents the onset, alleviates the symptoms, or stops the progression of a bacterial infection. In a preferred embodiment, a subject is a human or other animal patient in need of lipopeptide treatment. An established infection may be one that is acute or chronic. An effective dose is generally between about 0.1 and about 75 mg/kg crystalline or crystal-like lipopeptide, such as crystalline or crystal-like daptomycin or daptomycin-related lipopeptide, or a pharmaceutically acceptable salt thereof. A preferred dose is from about 1 to about 25 mg/kg of crystalline or crystal-like daptomycin or daptomycin-related lipopeptide or a pharmaceutically acceptable salt thereof. A more preferred dose is from about 1 to 12 mg/kg crystalline or crystal-like daptomycin, a crystalline or crystal-like daptomycin-related lipopeptide or a pharmaceutically acceptable salt thereof. An even more preferred dose is about 3 to 8 mg/kg crystalline or crystal-like daptomycin or daptomycin-related lipopeptide or a pharmaceutically acceptable salt thereof. Exemplary procedures for delivering an antibacterial agent are described in U.S. Pat. No. 5,041,567, issued to Rogers and in International PCT Publication WO 95/05384, the entire contents of which documents are incorporated in their entirety herein by reference.

The crystalline or crystal-like lipopeptide, e.g., daptomycin, can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the lipopeptide and the microorganism or microorganisms involved in the infection. A method of administration is disclosed in WO 00/18419, published Apr. 6, 2000, herein incorporated by reference.

The methods of the present invention comprise administering a compound of the invention, or a pharmaceutical composition thereof to a patient in need thereof in an amount that is efficacious in reducing or eliminating the gram-positive bacterial infection. The lipopeptide may be administered orally, parenterally, by inhalation, topically, rectally, nasally, buccally, vaginally, or by an implanted reservoir, external pump or catheter. The lipopeptide may be prepared for ophthalmic or aerosolized uses. Compounds of the invention, or pharmaceutical compositions thereof also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In a preferred embodiment, crystalline or crystal-like daptomycin, daptomycin-related lipopeptide or other lipopeptide is administered intravenously, subcutaneously or orally.

The method of the instant invention may be used to treat a patient having a bacterial infection in which the infection is caused or exacerbated by any type of gram-positive bacteria. In a preferred embodiment, crystalline or crystal-like daptomycin, daptomycin-related lipopeptide or other lipopeptide, or pharmaceutical compositions thereof, are administered to a patient according to the methods of this invention. In another embodiment, the bacterial infection may be caused or exacerbated by bacteria including, but not limited to, methicillin-susceptible and methicillin-resistant staphylococci (including *Staphylococcus aureus, Staphylococcus epidermidis, Staphylococcus haemolyticus, Staphylococcus hominis, Sta-*

*phylococcus saprophyticus*, and coagulase-negative staphylococci), glycopeptide intermediary-susceptible *Staphylococcus aureus* (GISA), penicillin-susceptible and penicillin-resistant streptococci (including *Streptococcus pneumoniae, Streptococcus pyogenes, Streptococcus agalactiae, Streptococcus avium, Streptococcus bovis, Streptococcus lactis, Streptococcus sangius* and Streptococci Group C, Streptococci Group G and viridans streptococci), enterococci (including vancomycin-susceptible and vancomycin-resistant strains such as *Enterococcus faecalis* and *Enterococcus faecium*), *Clostridium difficile, Clostridium clostridiiforme, Clostridium innocuum, Clostridium perfringens, Clostridium ramosum, Haemophilus influenzae, Listeria monocytogenes, Corynebacterium jeikeium, Bifidobacterium* spp., *Eubacterium aerofaciens, Eubacterium lentum, Lactobacillus acidophilus, Lactobacillus casei, Lactobacilllus plantarum, Lactococcus* spp., *Leuconostoc* spp., *Pediococcus, Peptostreptococcus anaerobius, Peptostreptococcus asaccarolyticus, Peptostreptococcus magnus, Peptostreptococcus micros, Peptostreptococcus prevotii, Peptostreptococcus productus, Propionibacterium acnes*, and *Actinomyces* spp.

The antibacterial activity of daptomycin against classically "resistant" strains is comparable to that against classically "susceptible" strains in in vitro experiments. In addition, the minimum inhibitory concentration (MIC) value for daptomycin against susceptible strains is typically 4-fold lower than that of vancomycin. Thus, in a preferred embodiment, a compound of the invention, or a pharmaceutical composition of any one of these crystalline or crystal-like lipopeptides, is administered according to the methods of this invention to a patient who exhibits a bacterial infection that is resistant to other antibiotics, including vancomycin. In addition, unlike glycopeptide antibiotics, daptomycin exhibits rapid, concentration-dependent bactericidal activity against gram-positive organisms. Thus, in a preferred embodiment, compounds of the invention, or a pharmaceutical composition of any one of these crystalline or crystal-like lipopeptides, is administered according to the methods of this invention to a patient in need of rapidly acting antibiotic therapy.

The method of the instant invention may be used for a gram-positive bacterial infection of any organ or tissue in the body. These organs or tissue include, without limitation, skeletal muscle, skin, bloodstream, kidneys, heart, lung and bone. The method of the invention may be used to treat, without limitation, skin and soft tissue infections, bacteremia and urinary tract infections. The method of the invention may be used to treat community acquired respiratory infections, including, without limitation, otitis media, sinusitis, chronic bronchitis and pneumonia, including pneumonia caused by drug-resistant *Streptoococcus pneumoniae* or *Haemophilus influenzae*. The method of the invention also may be used to treat mixed infections that comprise different types of gram-positive bacteria, including aerobic, caprophilic or anaerobic bacteria. These types of infections include intra-abdominal infections, pneumonia, bone and joint infections and obstetrical/gynecological infections. The method of the invention also may be used to treat an infection including, without limitation, endocarditis, nephritis, septic arthritis and osteomyelitis. In a preferred embodiment, any of the above-described diseases may be treated using crystalline or crystal-like daptomycin, daptomycin-related lipopeptide, antibacterial lipopeptide, or pharmaceutical compositions of any one of these crystalline or crystal-like lipopeptides.

Crystalline or crystal-like daptomycin, daptomycin-related lipopeptide or other lipopeptide may also be administered in the diet or feed of a patient or animal. If administered as part of a total dietary intake, the amount of daptomycin or other lipopeptide can be less than 1% by weight of the diet and preferably no more than 0.5% by weight. The diet for animals can be normal foodstuffs to which daptomycin or other lipopeptide can be added or it can be added to a premix.

The method of the instant invention may also be practiced while concurrently administering another form of daptomycin or other lipopeptide antibiotic, e.g., one that is not crystalline or crystal-like, or with one or more antifungal agents and/or one or more antibiotics other than crystalline or crystal-like daptomycin or other crystalline or crystal-like lipopeptide antibiotics. Co-administration of an antifungal agent and an antibiotic other than crystalline or crystal-like daptomycin or another lipopeptide antibiotic may be useful for mixed infections such as those caused by different types of gram-positive bacteria, or those that caused by both bacteria and fungus. Furthermore, crystalline or crystal-like daptomycin or other lipopeptide antibiotic may improve the toxicity profile of one or more co-administered antibiotics. It has been shown that administration of daptomycin and an aminoglycoside may ameliorate renal toxicity caused by the aminoglycoside. In a preferred embodiment, an antibiotic and/or antifungal agent may be administered concurrently with a compound of this invention, or in a pharmaceutical composition comprising a compound of this invention.

Antibacterial agents and classes thereof that may be co administered with a compound of the present invention include, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-amino salicylic acid (PAS), cycloserine, capreomycin, ethionamide, prothionamide, thiacetazone, viomycin, everninomycin, glycopeptide, glycylcylcline, ketolides, oxazolidinone; imipenen, amikacin, netilmicin, fosfomycin, gentamicin, ceftriaxone, Ziracin, LY 333328, CL 331002, HMR 3647, Linezolid, Synercid, Aztreonam, and Metronidazole, Epiroprim, OCA__983, GV__143253, Sanfetrinem sodium, CS__834, Biapenem, A__99058.1, A__165600, A__179796, KA 159, Dynemicin A, DX8739, DU 6681; Cefluprenam, ER 35786, Cefoselis, Sanfetrinem celexetil, HGP__31, Cefpirome, HMR__3647, RU__59863, Mersacidin, KP 736, Rifalazil; Kosan, AM 1732, MEN 10700, Lenapenem, BO 2502A, NE__1530, PR 39, K130, OPC 20000, OPC 2045, Veneprim, PD 138312, PD 140248, CP 111905, Sulopenem, ritipenam acoxyl, RO__65__5788, Cyclothialidine, Sch__ 40832, SEP__132613, micacocidin A, SB__275833, SR__15402, SUN A0026, TOC 39, carumonam, Cefozopran, Cefetamet pivoxil, and T 3811.

In a preferred embodiment, antibacterial agents that may be co administered with a compound according to this invention include, without limitation, imipenen, amikacin, netilmicin, fosfomycin, gentamicin, ceftriaxone, teicoplanin, Ziracin, LY 333328, CL 331002, HMR 3647, Linezolid, Synercid, Aztreonam, and Metronidazole.

Antifungal agents that may be co administered with a compound according to this invention include, without limitation, Caspofungen, Voriconazole, Sertaconazole, IB__367, FK__463, LY__303366, Sch__56592, Sitafloxacin, DB__289 polyenes, such as Amphotericin, Nystatin, Primaricin; azoles, such as Fluconazole, Itraconazole, and Ketoconazole;

allylamines, such as Naftifine and Terbinafine; and anti-metabolites such as Flucytosine. Other antifungal agents include without limitation, those disclosed in Fostel et al., Drug Discovery Today 5:25_32 (2000), herein incorporated by reference. Fostel et al. disclose antifungal compounds including Corynecandin, Mer_WF3010, Fusacandins, Artrichitin/LL 15G256(, Sordarins, Cispentacin, Azoxybacillin, Aureobasidin and Khafrefungin.

Compounds of this invention, or a pharmaceutical composition of any one or more of these crystalline or crystal-like lipopeptides, may be administered according to this method until the bacterial infection is eradicated or reduced. In one embodiment, the crystalline or crystal-like lipopeptide is administered for a period of time from approximately 3 days to approximately 6 months. In a preferred embodiment, the crystalline or crystal-like lipopeptide is administered for 7 to 56 days. In a more preferred embodiment, the crystalline or crystal-like lipopeptide is administered for 7 to 28 days. In an even more preferred embodiment, the crystalline or crystal-like lipopeptide is administered for 7 to 14 days. The crystalline or crystal-like lipopeptide may be administered for a longer or shorter time period if it is so desired. In a preferred embodiment, the lipopeptide is daptomycin or daptomycin-related lipopeptide.

In order that this invention may be more fully understood, the following examples are set forth. These examples are for the purpose of illustration only and are not to be construed as limiting the scope of the invention in any way.

Example 1

Daptomycin was prepared by conventional techniques. The daptomycin preparation was a pale yellow amorphous powder, with a solubility at 25° C. of greater than 1 g/mL in water and a solubility of 2.8 mg/mL in ethanol. The amorphous daptomycin preparation was hygroscopic and decomposed at 215° C.

The remaining examples describe crystallizing or precipitating lipopeptides in the presence or absence of an organic precipitant (e.g., PEG).

Example 2

In a microbatch crystallization, 25 µL of a daptomycin stock (20 mg/mL in methanol) was sequentially mixed with 15 µL of reagent stock (200 mM calcium acetate, 0.1 M cacodylate (pH 6.5), 18% [w/v] PEG 8000 and 15 µL ethylene glycol) to give a solution that was 27.5% aqueous component, 45% methanol and 27.5% ethylene glycol. Urchin-like crystals were formed at a yield of 50% with a purity of 98% as measured by HPLC.

Example 3

A daptomycin stock was prepared by dissolving 440 mg daptomycin in 1 mL of a buffer containing 25 mM sodium acetate (pH 5.0) and 5 mM $CaCl_2$. Crystallization was done by the vapor diffusion (hanging drop) method, in which 5 µL of the daptomycin stock was added to 5 µL of 0.1 M tri-sodium citrate dihydrate (pH 5.6), and 35% [v/v] tert-butanol in water to form a drop. The drop was suspended over a reservoir solution (0.1 M tri-sodium citrate dihydrate (pH 5.6), and 35% [v/v] tert-butanol in water) in an air-tight environment until crystallization occurred. This method yielded urchin-like daptomycin crystals. See, e.g., FIG. 2.

Example 4

5 µL of a daptomycin stock prepared as in Example 3 was added to 5 µL of a solution containing 0.1 M sodium cacodylate (pH 6.5), 0.2 M calcium acetate and 9% [w/v] PEG 8000. Crystallization was done by the vapor diffusion method as described in Example 3. This method yielded needle-like daptomycin crystals. See, e.g., FIG. 3.

Example 5

5 µL of a daptomycin stock prepared as in Example 3 was added to 5 µL of a solution of 0.1 M sodium cacodylate (pH 6.5), 0.2 M zinc acetate and 9% [w/v] PEG 8000 containing 0.1 µL benzamidine to give a final concentration of 220 mg/mL daptomycin. Crystallization was done by the vapor diffusion method as described in Example 3. This method yielded rod-like daptomycin crystals. See, e.g., FIG. 4.

Example 6

One mL of daptomycin (97.1% pure as determined by HPLC) at a concentration of 20-25 mg/mL in water was sequentially mixed with 231 µL water, 77 µL of calcium acetate (pH 6.0), 960 µL propylene glycol and 231 µL of 50% [w/v] PEG 4000. The solution was allowed to sit for 4-5 hours at 4° C. Urchin-like crystals were formed at a yield of 75%. The crystalline daptomycin was washed with isopropanol. The daptomycin was 98.4% pure as determined by HPLC.

Example 7

Daptomycin (200 mg, 97.1% pure) was dissolved in 2.54 mL water. The daptomycin solution was sequentially mixed in order with 10.0 mL methanol, 0.78 mL 1 M calcium acetate (pH 6.0), 9.50 mL propylene glycol and 2.20 mL 50% [w/v] PEG 4000 to give a final volume of 25.02 mL. The mixture was tumbled at room temperature for 10-14 hours in a hematology mixer (Fischer). Crystals began to appear within a few hours. Final yield was approximately 70-80% after 14 hours. The crystals were harvested by centrifugation at 1000 rpm for 15 minutes. The supernatant was removed and the crystals were resuspended in 12.5 mL isopropanol. The daptomycin suspension was transferred to a column (Biorad) and the isopropanol was removed by allowing it to drip by gravity. The crystals were dried by a nitrogen stream. Any lumps were broken up during the drying procedure to obtain a uniform dry sample. Crystals prepared by this method were urchin-like and had a purity of 98.37%.

Example 8

Daptomycin was crystallized according to Example 7 except that PEG 8000 was used in replacement of PEG 4000. The quantities of reagents used are identical to those in Example 7. Crystals prepared by this method were urchin-like and had a purity of 98.84%.

Example 9

Two daptomycin samples prepared according to Example 7 and one amorphous sample were analyzed for crystallinity using the USP <695> crystallinity test. Daptomycin particles were mounted in mineral oil on a glass slide and then were examined by polarizing light microscope (PLM). The particles were determined to be crystalline if they were birefringent (have interference colors) and had extinction positions when the stage was rotated.

The amorphous daptomycin sample consisted of lacy, flaky particles that were not birefringent. There were a few sliver-like areas in some of the flakes that had weak birefringence, but the particles were primarily amorphous. In contrast, the daptomycin samples prepared according to Example 7 consisted of polycrystalline particles with weak birefringence and some extinction, indicating that they were primarily crystalline. See FIG. 5.

Example 10

Two daptomycin samples prepared according to Example 7 and one amorphous sample were analyzed for crystallinity by x-ray powder diffraction. The samples were analyzed on a Siemens D500 Automated Powder Diffractometer (ORS 1D No. LD-301-4), which was operated according to ORS Standard Operation Procedure EQ-27 Rev. 9. The diffractometer was equipped with a graphite monochromator and a Cu ($\lambda$=1.54 Å) x-ray source operated at 50 kV, 40 mA. Two-theta ($\Theta$) calibration is performed using an NBS mica standard (SRM675). The samples were analyzed using the following instrument parameters:

| | |
|---|---|
| Measuring Range for 2Θ (degrees) | 4.0-40.0 |
| Step Width (degrees) | 0.05 |
| Measuring Time per Step (secs) | 1.2 |
| Beam Slits | 1(1°), 2(1°), 3(1°), 4(0.15°), 5(0.15°). |

Sample preparation was performed according to ORS Standard Operation Procedure MIC-7 Rev. 1 using a zero background sample plate.

All samples were done using a Cu ($\lambda$=1.54 Å) x-ray source. The amorphous daptomycin sample did not show any peaks by x-ray powder diffraction. See FIG. 6. In contrast, the two daptomycin samples both showed peaks by x-ray powder diffraction. The diffraction angle (2Θ) of the first daptomycin sample (FIG. 7) was 19.225, 23.242, 23.427 and 23.603 (degree). The diffraction angle (2Θ) for the second daptomycin sample (FIG. 8) was 10.966, 19.205 and 23.344 (degree). The first crystalline daptomycin sample also showed a small peak between 10-11°. See FIG. 7.

Example 11

Daptomycin was dissolved in water. Sodium acetate was added to achieve a final concentration of 187 mM. Calcium chloride was added to achieve a final concentration of 28 mM. The daptomycin solution was mixed and isopropanol was added to a final concentration of 78.4%. The solution was mixed and incubated. A precipitated material was formed after incubation. The precipitated material appeared to be urchin-like crystals of approximately 60 µm diameter by optical microscopy. The material was then dried. The dry material contained approximately 30-40% salt. After drying, powder x-ray diffraction was performed. The powder x-ray diffraction did not show the presence of crystals in the dried daptomycin precipitate.

Example 12

One gram of daptomycin (approximately 91.5% purity as measured by HPLC) was added to 16.8 mL of distilled water and dissolved. 2.5 mL of 1M calcium acetate (pH 6.1) and 60 mL of isopropanol was added. The solution was placed in a 27° C. water bath and permitted to equilibrate to temperature of the water bath. 5 mL aliquots of isopropanol were slowly added until the solution became cloudy (a total of approximately 30 mL isopropanol). The solution was incubated overnight at 27° C. to form a precipitate. The precipitate appeared to contain urchin-like crystals of approximately 60 µm by optical microscopy. See FIG. 2.

The daptomycin precipitate was poured into a pressure filter/drying funnel and filtered by gravity. The precipitate was washed twice with 25 mL each time of a washing solution (80% isopropanol and 20% solution A where solution A consists of 18 mL of water and 2 mL of glacial acetic acid) and allowed to drip by gravity overnight. The precipitate was then transferred to a desiccator and dried under vacuum. After drying, powder x-ray diffraction was performed. The powder x-ray diffraction did not show the presence of crystals in the dried daptomycin precipitate. However, purity analysis of the precipitated material by HPLC showed that the material was 98.2% pure daptomycin. Significantly, the daptomycin preparation after precipitation has significantly less anhydrodaptomycin than the daptomycin preparation before precipitation.

Figure 3:
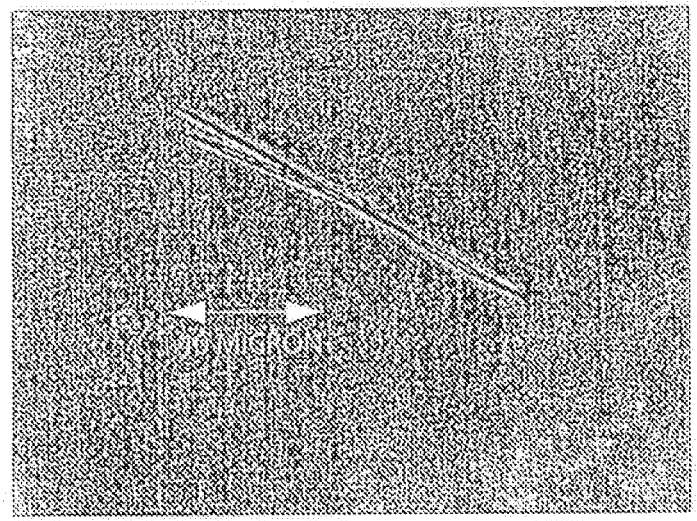
FIG. 3 shows a photomicrograph of needle-like crystals of daptomycin.
Figure 4:
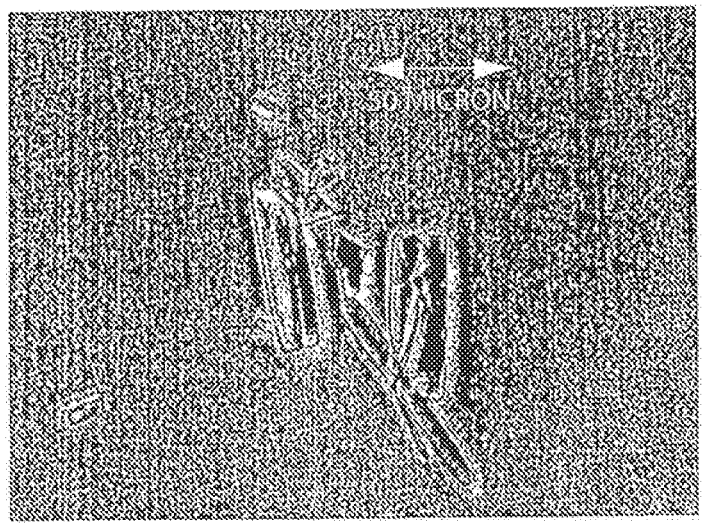
FIG. 4 shows a photomicrograph of rod-like crystals of daptomycin.
Figure 5C:
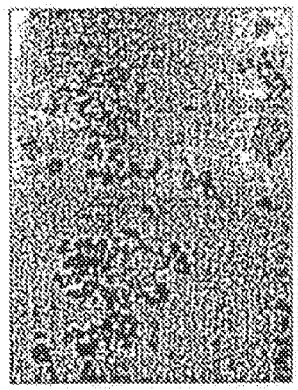
FIG. 5 shows photomicrographs of daptomycin samples at 100× magnification. Photomicrographs of amorphous daptomycin are shown using plane transmitted light (A) and using crossed polarized light (B). Photomicrographs of daptomycin crystals are shown using plane transmitted light (C and E) and using crossed polarized light (D and F). The daptomycin crystals were produced by the protocol disclosed in Example 7.
Figure 5F:
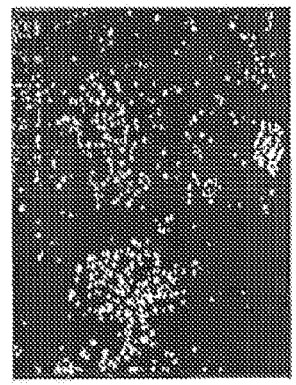
Figure 5B:
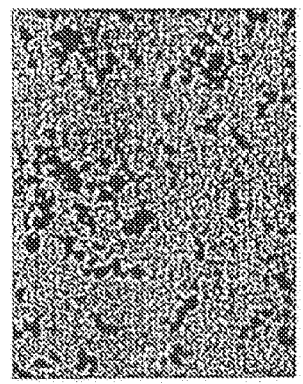
Figure 5E:
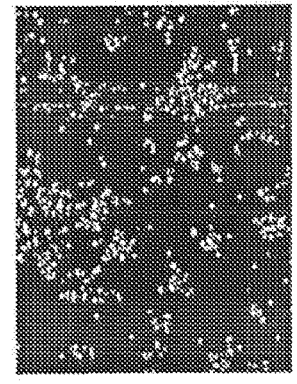
Figure 5A:
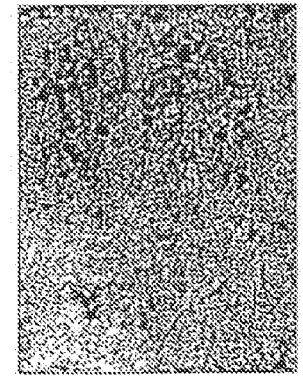
Figure 5D:
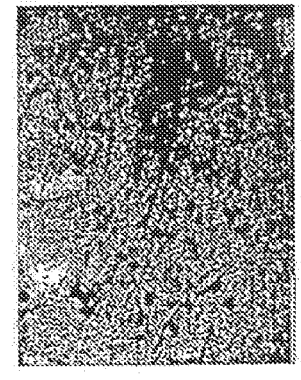

Without wishing to be bound by any theory, applicants believe that the conditions used to precipitate the daptomycin in Examples 11 and 12 actually produce a crystalline form of daptomycin but that the subsequent washing steps and/or drying steps cause the crystalline daptomycin to revert to a non-crystalline form. Nonetheless, the non-crystalline daptomycin is still crystal-like as shown in FIG. 3 by the birefringence of a crystal sample in polarized light.

Example 13

A fermentation culture of *S. roseosporus* NRRL Strain 15998 is conducted in a controlled decanoic acid feed fermentation at levels that optimize the production of the antibiotic while minimizing the production of contaminants. The residual decanoic acid feed is measured by gas chromatography and the target residual level is 10 ppm decanoic acid from the start of induction (approximately at hour 30) until harvest. Centrifugation of the culture and subsequent analysis of the clarified broth are used to measure the production of daptomycin by HPLC. The harvest titer is typically between 1.0 and 3.0 grams per liter of fermentation broth.

The fermentation culture is harvested either by microfiltration using a Pall-Sep or equivalent microfiltration system, or by full commercial-scale centrifugation and depth filter. The clarified broth is applied to an anion exchange resin, Mitsubishi FP-DA 13, washed with of 30 mM NaCl at pH 6.5 and eluted with of 300 mM NaCl at pH 6.0-6.5. Alternatively, the FP-DA 13 column is washed with of 30 mM NaCl at pH 6.5 and eluted with of 300 mM NaCl at pH 6.0-6.5. The pH is adjusted to 3.0-4.8 and the temperature is adjusted to 2-15° C. Under these conditions, daptomycin forms a micelle. The micellar daptomycin solution is filtered-washed using a 10,000 NMW ultrafilter (AG Technology Corp. UF hollow fiber or equivalent) in any configuration. The daptomycin micelles are retained by the filter, but a large number of impurities are eliminated because they pass through the 10,000 NMW filter. Ultrafiltration of daptomycin micelles increases daptomycin purity to approximately 80-90%.

Figure 9:
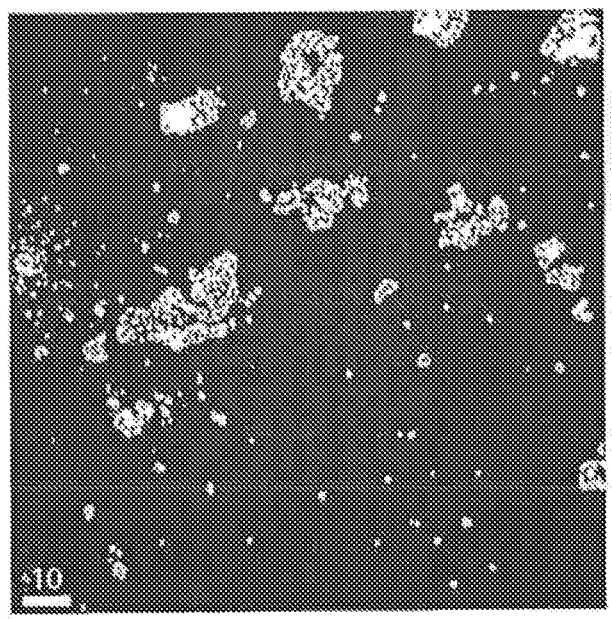
FIG. 9 shows birefringence of a crystal-like particle of daptomycin when exposed to polarized light. The crystal-like particle was produced by the method described in Example 12.

The daptomycin preparation is then crystallized or precipitated under sterile conditions using one of the methods described above. In a preferred embodiment, the daptomycin is crystallized or precipitated according to the protocol described in Examples 7, 8 or 12 except that it can be scaled up for large preparation of daptomycin. The crystalline or crystal-like daptomycin is separated from the crystallization/precipitation solution by filtration, preferably by vacuum filtration. The crystalline or crystal-like daptomycin is washed with washing solution (see Example 3). The crystalline or crystal-like daptomycin is then vacuum dried under sterile conditions using a 0.65 m³ Klein Hastelloy-B double cone vacuum dryer or equivalent apparatus. Vials are then filled with either 250 or 500 mg of dried crystalline daptomycin per vial. FIG. 9 shows a flowchart of this manufacturing method.

Example 14

Fermentation of *S. roseosporus*, microfiltration of the fermentation culture and anion exchange chromatography is performed as described in Example 13. The daptomycin preparation is approximately 35-40% pure at this point. After anion exchange chromatography, the daptomycin is crystallized or precipitated according to the protocol described in Example 13. The daptomycin is then washed and dried according to the protocol set forth in Example 13. The dried crystalline or crystal-like daptomycin is then used to fill sterile vials as described in Example 13. FIG. 6 shows a flowchart of this manufacturing method.

Example 15

Fermentation of *S. roseosporus* and microfiltration of the fermentation culture is performed as described in Example 13. After microfiltration, the fermentation culture is subjected to size exclusion ultrafiltration as described in Example 13. The daptomycin preparation is approximately 35-40% pure at this point. After ultrafiltration, the daptomycin is crystallized or precipitated according to the protocol described in Example 13. The daptomycin is then washed and dried according to the protocol set forth in Example 13. The dried crystalline or crystal-like daptomycin is then used to fill sterile vials as described in Example 13. FIG. 7 shows a flowchart of this manufacturing method.

Example 16

Fermentation of *S. roseosporus* and microfiltration of the fermentation culture is performed as described in Example 13. The daptomycin preparation is 5-10% pure at this point. After microfiltration, the fermentation culture is crystallized or precipitated according to the protocol described in Example 13. The daptomycin is then washed and dried and used to fill sterile vials as described in Example 13. FIG. 8 shows a flowchart of this manufacturing method.

Example 17

CB-131547 (see FIG. x), a cyclic lipopeptide analog of daptomycin, was prepared via a semi-synthesis route from daptomycin. The CB-131547 was a pale yellow amorphous powder, with a solubility at 25° C. of ~80 mg/mL in normal saline.

CB-131547 (60 mg, ~90% pure) is dissolved in 2.5 mL water. The CB-131547 solution is sequentially mixed in order with 5.0 mL methanol, 0.2 mL 1 M calcium acetate (pH 6.0), 2.5 mL propylene glycol, and 1.0 mL 50% (w/v) PEG 4000 to give a final volume of 11.2 mL. The solution is allowed to sit for 4 to 24 hours at 4° C. CB-131547 crystals are formed at a yield of ~70% with a purity ~98.0% as determined by HPLC.

Example 18

CB-131547 (see FIG. x), a cyclic lipopeptide analog of daptomycin, was prepared via a semi-synthesis route from daptomycin. The CB-131547 was a pale yellow amorphous powder, with a solubility at 25° C. of ~80 mg/mL in normal saline.

CB-131547 (60 mg, ~90% pure) is dissolved in 2.5 mL water. 0.2 mL 1 M calcium acetate (pH 6.0) and 8 mL of isopropanol is added. The solution is allowed to equilibrate at room temperature (25° C.) for 5 minutes. One mL aliquots of isopropanol are slowly added until the solution becomes cloudy. The solution is stored at room temperature overnight to form crystals.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:
1. A method comprising the steps of:
   a) combining daptomycin in a solution comprising tert-butanol and a salt selected from the group consisting of calcium chloride and zinc acetate, at a pH of about 5.5 to 7.5 and a temperature of about 0 to 30 degrees C.;
   b) allowing the daptomycin to precipitate or crystallize from the solution; and
   c) obtaining a purified daptomycin from the precipitated or crystallized daptomycin.
2. The method of claim 1, wherein the temperature of the solution is about 20 to 30 degrees C.
3. The method of claim 1, wherein the alcohol is tert-butanol, the pH of the solution is 5.5-7.5 and the temperature of the solution is about 20 to 30 degrees C.
4. The method of claim 1, wherein the salt is calcium chloride.
5. The method of claim 1, wherein the precipitated or crystallized daptomycin is a calcium daptomycin salt.
6. The method of claim 1, wherein the daptomycin is precipitated or crystallized at a pH of about 5.9 to 6.3 at a temperature of about 24 to 28 degree C., and the method further comprising the steps of:
   i) fermenting *Streptomyces roseosporus* to obtain a fermentation culture containing daptomycin;
   ii) clarifying the daptomycin from the fermentation culture to obtain a daptomycin preparation;
   iii) subjecting the daptomycin preparation to size exclusion ultrafiltration to obtain a filtered daptomycin preparation;
   iv) subjecting the filtered daptomycin preparation to hydrophobic interaction chromatography;
   v) subjecting the daptomycin from the hydrophobic interaction chromatography to anionic exchange chromatography;
   vi) forming daptomycin micelles from the daptomycin obtained from the anion exchange chromatography;
   vii) filtering the daptomycin micelles under conditions in which the daptomycin micelles are retained on the filter; and
   viii) forming the solution containing the daptomycin from the daptomycin micelles.
7. A method comprising the steps of:
   a) forming a daptomycin preparation containing daptomycin micelles,
   b) filtering the daptomycin micelles under conditions in which the daptomycin micelles are retained on the filter;

c) forming a solution containing the daptomycin from the daptomycin micelles, tert-butanol and a salt selected from the group consisting of calcium chloride and zinc acetate;

d) maintaining the daptomycin from the solution in step c) at a temperature of about 0 to 30 degrees C. and a pH of about 5.5 to 7.5 to form precipitated or crystalline daptomycin; and e) collecting the precipitated or crystalline daptomycin.

8. The method of claim 7, wherein the temperature of the solution is about 20 to 30 degrees C.

9. The method of claim 7, wherein the alcohol is tert-butanol, the pH of the solution is about 5.6 and the temperature of the solution is about 20 to 30 degrees C.

10. The method of claim 7, wherein the daptomycin preparation is obtained by a process comprising the step of fermenting *Streptomyces roseosporus* to obtain a fermentation culture containing the daptomycin.

11. The method of claim 10, wherein the daptomycin preparation is obtained by a process further comprising the steps of:

i) clarifying the daptomycin from the fermentation culture to obtain a daptomycin preparation; and ii) subjecting the filtered daptomycin preparation to at least one of hydrophobic interaction chromatography and anion exchange chromatography.

12. The method of claim 11, wherein the daptomycin micelles are formed by altering at least one of the pH, temperature and salt concentration of the daptomycin obtained from the hydrophobic interaction chromatography or the anion exchange chromatography to form the daptomycin micelles.

13. The method of claim 12, wherein the daptomycin from the solution in step c) is maintained at a temperature of about 20 to 30 degrees C. and a pH of about 5.9 to 6.3.

14. A method of manufacturing daptomycin, the method comprising the steps of:

a) fermenting *Streptomyces roseosporus* to obtain a fermentation culture containing daptomycin;

b) clarifying the daptomycin from the fermentation culture to obtain a daptomycin preparation;

c) subjecting the daptomycin preparation to size exclusion ultrafiltration to obtain a filtered daptomycin preparation;

d) subjecting the filtered daptomycin preparation to hydrophobic interaction chromatography;

e) subjecting the daptomycin obtained from the hydrophobic interaction chromatography to anion exchange chromatography;

f) altering at least one of the pH, temperature and salt concentration of the daptomycin obtained from the anion exchange chromatography to form daptomycin micelles;

g) filtering the daptomycin micelles under conditions in which the daptomycin micelles are retained on the filter; and h) forming a solution containing the daptomycin from the daptomycin micelles, tert-butanol and a salt selected from the group consisting of calcium chloride and zinc acetate;

i) precipitating or crystallizing daptomycin from the solution at a temperature of about 0 to 30 degrees C. and a pH of about 5.5 to 7.5; and j) collecting the precipitated or crystallized daptomycin from the solution.

15. The method of claim 14, wherein the temperature of the solution is about 20 to 30 degrees C.

16. The method of claim 14, wherein the alcohol is tert-butanol, the pH of the solution is about 5.6 and the temperature of the solution is about 20 to 30 degrees C.

17. The method of claim 14, wherein the salt is zinc acetate.

18. The method of claim 14, wherein the salt is calcium chloride.

19. The method of claim 18 wherein the precipitated or crystallized daptomycin is a calcium daptomycin salt.

20. The method of claim 19, wherein the daptomycin is precipitated or crystallized from the solution at a temperature of about 20 to 30 degrees C. and a pH of about 5.9 to 6.3.

* * * * *